US008415132B2

(12) United States Patent
Djurup et al.

(10) Patent No.: US 8,415,132 B2
(45) Date of Patent: *Apr. 9, 2013

(54) PURIFICATION OF VACCINIA VIRUS- AND RECOMBINANT VACCINIA VIRUS-BASED VACCINES

(75) Inventors: Rene Djurup, Gentofte (DK); Sara Post Hansen, Hoersholm (DK)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/214,836

(22) Filed: Aug. 22, 2011

(65) Prior Publication Data

US 2011/0312060 A1    Dec. 22, 2011

Related U.S. Application Data

(63) Continuation of application No. 12/622,474, filed on Nov. 20, 2009, now Pat. No. 8,003,363, which is a continuation-in-part of application No. 12/598,362, filed as application No. PCT/EP2008/003679 on May 7, 2008, now Pat. No. 8,012,738.

(60) Provisional application No. 60/924,413, filed on May 14, 2007.

(51) Int. Cl.
*C12N 7/02* (2006.01)
*A61K 39/285* (2006.01)

(52) U.S. Cl. .................. 435/239; 424/199.1; 424/232.1

(58) Field of Classification Search ........................ None
See application file for complete search history.

(56) References Cited

U.S. PATENT DOCUMENTS

| 6,267,967 | B1 | 7/2001 | Johnston | |
|---|---|---|---|---|
| 8,003,363 | B2 * | 8/2011 | Djurup et al. | 435/239 |
| 8,003,364 | B2 * | 8/2011 | Post Hansen et al. | 435/239 |
| 8,163,531 | B2 * | 4/2012 | Post Hansen et al. | 435/239 |
| 2003/0165477 | A1 | 9/2003 | Balloul | |
| 2004/0175398 | A1 * | 9/2004 | Moyer | 424/232.1 |
| 2007/0071769 | A1 | 3/2007 | Sutter | |

FOREIGN PATENT DOCUMENTS

WO    WO03/054175 A1    7/2003

OTHER PUBLICATIONS

O'Keeffe et al (Biotechnology and Bioengineering 62:537-545, 1999).*
Chung et al (Journal of Virology 72:1577-1585, 1998).*
Baba et al., Sulfated Polysaccharides Are Potent and Selective Inhibitors of Various Enveloped Viruses, Including Herpes Simplex Virus, Cytomegalovirus, Vesicular Stomatitis Virus, and Human Immunodeficiency Virus, Antimicrobial Agents and Chemotherapy 32 (1988) 1742-1745.
Chattopadhyay et al., Polysaccharides from *Gracilaria corticata*: Sulfation, chemical characterization and anti-HSV activities, International Journal of Biological Macromolecules 43 (2008) 346-351.

Enden et al., A model of the dynamics of insect cell infection at lowmultiplicity of infection, Journal of Theoretical Biology 237 (2005) 257-264.
Ho et al., The Oligomeric Structure of Vaccinia Viral Envelope Protein A27L is Essential for Binding to Heparin and Heparan Sulfates on Cell Surfaces: A Structural and Functional Approach Using Site-specific Mutagenesis, J. Mol. Biol. (2005) 349, 1060-1071.
Hsaio et al., Cell Surface Proteoglycans Are Necessary for A27L Protein-Mediated Cell Fusion: Identification of the N-Terminal Region of A27L Protein as the Glycosaminoglycan-Binding Domain, Journal of Virology 72 (1998) 8374-8379.
Hsaio et al., Vaccinia Virus Envelope D8L Protein Binds to Cell Surface Chondroitin Sulfate and Mediates the Adsorption of Intracellular Mature Virions to Cells, Journal of Virology 73 (1999) 8750-8761.
Kalbfuss et al., Purification of Cell Culture-Derived Human Influenza A Virus by Size-Exclusion and Anion-Exchange Chromatography, Biotechnology and Bioengineering 96 (2007) 932-944.
Lin et al., Vaccinia Virus Envelope H3L Protein Binds to Cell Surface Heparan Sulfate and Is Important for Intracellular Mature Virion Morphogenesis and Virus Infection In Vitro and In Vivo, Journal of Virology 74 (2000) 3353-3365.
Lycke et al., Binding of herpes simplex virus to cellular heparan sulphate, an initial step in the adsorption process, Journal of General Virology (1991) 72, 1131-1137.
Mitsuya et al., Dextran Sulfate Suppression of Viruses in the HIV Family: Inhibition of Virion Binding to CD4+ Cells, Science 240 (1988) 646-649.
O'Keeffe et al., The Affinity Adsorptive Recovery of an Infectious Herpes Simplex Virus Vaccine, Biotechnology and Bioengineering 62 (1999) 537-545.
Opitz et al., Lectin-affinity chromatography for downstream processing of MDCK cell culture derived human influenza A viruses, Vaccine 25 (2007) 939-947.
Opitz et al., Sulfated Membrane Adsorbers for Economic Pseudo-Affinity Capture of Influenza Virus Particles, Biotechnology and Bioengineering 103 (2009) 1144-1154.
Peixoto et al., Towards Purification of Adenoviral Vectors Based on Membrane Technology, Biotechnol. Prog. 2008, 24, 1290-1296.
Piret et al., In Vitro and In Vivo Evaluations of Sodium Lauryl Sulfate and Dextran Sulfate as Microbicides against Herpes Simplex and Human Immunodeficiency Viruses, Journal of Clinical Microbiology 38 (2000) 110-119.
Resch et al., Protein composition of the vaccinia virus mature virion, Virology 358 (2007) 233-247.

(Continued)

*Primary Examiner* — Mary E Mosher
(74) *Attorney, Agent, or Firm* — Law Office of Salvatore Arrigo and Scott Lee, LLP

(57) ABSTRACT

The present invention relates to methods for purification of Vaccinia viruses (VV) and/or Vaccinia virus (VV) particles, which can lead to highly pure and stable virus preparations of predominantly biologically active viruses. The invention encompasses purifying a virus preparation in a sterilized way with high efficiency and desirable yield in terms of purity, biological activity and stability, aspects advantageous for industrial production.

24 Claims, 2 Drawing Sheets

OTHER PUBLICATIONS

Smith et al., The formation and function of extracellular enveloped vaccinia virus, Journal of General Virology (2002) 83, 2915-2931.

Wu et al., Ion-Exchange Membrane Chromatography Method for Rapid and Efficient Purification of Recombinant Baculovirus and Baculovirus gp64 Protein, Human Gene Therapy (2007) 18:665-672.

Harrer et al., Therapeutic vaccination of HIV-1-infected patients on HAART with a recombinant HIV-1 nef-expressing MVA: safety, immunogenicity and influence on viral load during treatment interruption, Antiviral Therapy 10:285-300 (2005).

Shen et al., Fighting Cancer with Vaccinia Virus: Teaching New Tricks to an Old Dog, Molecular Therapy 11:180-195 (2005).

Chung et al., A27L Protein Mediates Vaccinia Virus Interaction with Cell Surface Heparan Sulfate, Journal of Virology 72:1577-1585 (1998).

Zahn et al., Hepatitis C virus and hepatitis B virus bind to heparin: purification of largely IgG-free virions from infected plasma by heparin chromatography, J. Gen. Virology 86:677-685 (2005).

Broder et al., Recombinant Vaccinia Viruses, Molecular Biotechnology 13:223-245 (1999).

Wolff et al., Capturing of Cell Culture-Derived Modified Vaccinia Ankara Virus by Ion Exchange and Pseudo-Affinity Membrane Adsorbers, Biotechnology and Bioengineering 105: 761-769 (2010) [e-pub Nov. 4, 2009].

O'Neil et al., Virus Harvesting and Affinity-based Liquid Chromatograpy, Bio/Technology vol. 11:173-178 (1993).

* cited by examiner

PURIFICATION OF VACCINIA VIRUS- AND RECOMBINANT VACCINIA VIRUS-BASED VACCINES

CROSS-REFERENCE TO RELATED APPLICATIONS

This application is a continuation of U.S. application Ser. No. 12/622,474, filed Nov. 20, 2009, now U.S. Pat. No. 8,003,363, which is a continuation-in-part of U.S. application Ser. No. 12/598,362, filed Oct. 30, 2009 (now U.S. Pat. No. 8,012,738), which is the U.S. National Stage of International Application No. PCT/EP2008/003679 filed May 7, 2008, which claims the benefit of U.S. Provisional Application No. 60/924,413, filed May 14, 2007, all of which are incorporated herein by reference.

BACKGROUND OF THE INVENTION

1. Field of the Invention

The invention relates to methods for purification of Vaccinia viruses (VV) and/or Vaccinia virus (VV) particles.

2. Description of Related Art

Traditionally in medicine, a vector is a living organism that does not cause disease itself, but which spreads infection by "carrying" pathogens (agents that cause disease) from one host to another. A vaccine vector is a weakened or killed version of a virus or bacterium that carries an inserted antigen (coding for a protein recognized by the body as foreign) from a disease-causing agent to the subject being vaccinated. A vaccine vector delivers the antigen in a natural way into the body and stimulates the immune system into acting against a "safe infection." The immune system is led into generating an immune response against the antigen that protects the vaccinated subject against future "risky infections."

In vaccine development, a recombinant modified virus can be used as the vehicle or vaccine vector for delivering genetic material to a cell. Once in the cell, genetic information is transcribed and translated into proteins, including the inserted antigen targeted against a specific disease. Treatment is successful if the antigen delivered by the vector into the cell produces a protein, which induces the body's immune response against the antigen and thereby protects against the disease.

A viral vector can be based on an attenuated virus, which cannot replicate in the host but is able to introduce and express a foreign gene in the infected cell. The virus or the recombinant virus is thereby able to make a protein and display it to the immune system of the host. Some key features of viral vectors are that they can elicit a strong humoral (B-cell) and cell-mediated (T-cell) immune response.

Viral vectors are commonly used by researchers to develop vaccines for the prevention and treatment of infectious diseases and cancer, and of these, poxviruses (including canary pox, vaccinia, and fowl pox) are the most common vector vaccine candidates.

Pox viruses are a preferred choice for transfer of genetic material into new hosts due to the relatively large size of the viral genome (appr. 150/200 kb) and because of their ability to replicate in the infected cell's cytoplasm instead of the nucleus, thereby minimizing the risk of integrating genetic material into the genome of the host cell. Of the pox viruses, the vaccinia and variola species are the two best known. The virions of pox viruses are large as compared to most other animal viruses (for more details see Fields et al., eds., Virology, 3rd Edition, Volume 2, Chapter 83, pages 2637 if).

Variola virus is the cause of smallpox. In contrast to variola virus, vaccinia virus does not normally cause systemic disease in immune-competent individuals and it has therefore been used as a live vaccine to immunize against smallpox. Successful worldwide vaccination with Vaccinia virus culminated in the eradication of smallpox as a natural disease in the 1980s (The global eradication of smallpox. Final report of the global commission for the certification of smallpox eradication; History of Public Health, No. 4, Geneva: World Health Organization, 1980). Since then, vaccination has been discontinued for many years, except for people at high risk of poxvirus infections (for example, laboratory workers). However, there is an increasing fear that, for example, variola causing smallpox may be used as a bio-terror weapon. Furthermore, there is a risk that other poxviruses such as cowpox, camelpox, and monkeypox may potentially mutate, through selection mechanisms, and obtain similar phenotypes as variola. Several governments are therefore building up stockpiles of Vaccinia-based vaccines to be used either pre-exposure (before encounter with variola virus) or post-exposure (after encounter with variola virus) of a presumed or actual smallpox attack.

Vaccinia virus is highly immune-stimulating and provokes strong B- (humoral) and T-cell mediated immunity to both its own gene products and to any foreign gene product resulting from genes inserted in the Vaccinia genome. Vaccinia virus is therefore seen as an ideal vector for vaccines against smallpox and other infectious diseases and cancer in the form of recombinant vaccines. Most of the recombinant Vaccinia viruses described in the literature are based on the fully replication competent Western Reserve strain of Vaccinia virus. It is known that this strain has a high neurovirulence and is thus poorly suited for use in humans and animals (Morita et al. 1987, Vaccine 5, 65-70).

In contrast, the Modified Vaccinia virus Ankara (MVA) is known to be exceptionally safe. MVA has been generated by long-term serial passages of the Chorioallantois Vaccinia Ankara (CVA) strain of Vaccinia virus on chicken embryo fibroblast (CEF) cells (for review see Mayr, A. et al. 1975, Infection 3, 6-14; Swiss Patent No. 568,392). Examples of MVA virus strains deposited in compliance with the requirements of the Budapest Treaty are strains MVA 572, MVA 575, and MVA-BN® deposited at the European Collection of Animal Cell Cultures (ECACC), Salisbury (UK) with the deposition numbers ECACC V94012707, ECACC V00120707 and ECACC V00083008, respectively, and described in U.S. Pat. Nos. 7,094,412 and 7,189,536.

MVA is distinguished by its great attenuation profile compared to its precursor CVA. It has diminished virulence or infectiousness, while maintaining good immunogenicity. The MVA virus has been analyzed to determine alterations in the genome relative to the wild type CVA strain. Six major deletions of genomic DNA (deletion I, II, III, IV, V, and VI) totaling 31,000 base pairs have been identified (Meyer, H. et al. 1991, J. Gen. Virol. 72, 1031-1038). The resulting MVA virus became severely host-cell restricted to avian cells. The excellent properties of the MVA strain have been demonstrated in extensive clinical trials (Mayr, A. et al. 1978, Zbl. Bakt. Hyg. I, Abt. Org. B 167, 375-390; Stickl, H. et al. 1974, Dtsch. med. Wschr. 99, 2386-2392), where MVA 571 has been used as a priming vaccine at a low dose prior to the administration of conventional smallpox vaccine in a two-step program and was without any significant adverse events (SAES) in more than 120,000 primary vaccinees in Germany (Stickl, H et al. 1974, Dtsch. med. Wschr. 99, 2386-2392; Mayr et al. 1978, Zbl. Bakt. Hyg. I, Abt. Org. B 167, 375-390).

MVA-BN® is a virus used in the manufacturing of a standalone third generation smallpox vaccine. MVA-BN® was developed by further passages from MVA strain 571/572. To date, more than 1500 subjects including subjects with atopic dermatitis (AD) and HIV infection have been vaccinated in clinical trials with MVA-BN® based vaccines.

The renewed interest in smallpox vaccine-campaigns with Vaccinia-based vaccines has initiated an increased global demand for large-scale smallpox vaccine production. Furthermore, the use of Vaccinia virus as a tool for preparation of recombinant vaccines has additionally created significant industrial interest in methods for manufacturing (growth and purification) of native Vaccinia viruses and recombinant-modified Vaccinia viruses.

Viruses used in the manufacturing of vaccines or for diagnostic purposes can be purified in several ways depending on the type of virus. Traditionally, purification of pox viruses including Vaccinia viruses and recombinant-modified Vaccinia viruses has been carried out based on methods separating molecules by means of their size differences. To enhance removal of host cell contaminants (e.g. DNA and proteins), in particular DNA, the primary purification by means of size separation has been supplemented by secondary methods such as enzymatic digestion of DNA (e.g. Benzonase treatment). Most commonly, the primary purification of Vaccinia viruses and recombinant-modified Vaccinia viruses has been performed by sucrose cushion or sucrose gradient centrifugation at various sucrose concentrations. Recently, ultrafiltration has also been applied either alone or in combination with sucrose cushion or sucrose gradient purification.

Vaccinia Viruses-based vaccines have in general been manufactured in primary CEF (Chicken Embryo Fibroblasts) cultures. Vaccines manufactured in primary CEF cultures are generally considered safe as regards residual contaminants. First, it is scientifically unlikely that primary cell cultures from healthy chicken embryos should contain any harmful contaminants (proteins, DNA). Second, millions of people have been vaccinated with vaccines manufactured on CEF cultures without any adverse effects resulting from the contaminants (CEF proteins and CEF DNA). There is, therefore, no regulatory requirement for the level of host cell contaminants in vaccines manufactured in primary CEF cultures, but for each vaccine the manufacturer must document its safety. The regulatory concern for vaccines manufactured in primary CEF cultures relates to the risk of adventitious agents (micro-organisms (including bacteria, fungi, mycoplasma/spiroplasma, mycobacteria, rickettsia, viruses, protozoa, parasites, TSE agent) that are inadvertently introduced into the production of a biological product).

In the current methods for purification of Vaccinia viruses, manufactured in primary CEF culture the level of CEF protein may be up to 1 mg/dose and the CEF DNA level may exceed 10 μg/dose of $1\times10^8$ as measured by the TCID50. These levels are considered acceptable from a safety and regulatory perspective as long as the individual vaccine manufacturer demonstrates that the levels to be found in the Final Drug Product (FDP) are safe at the intended human indications. Due to the risk of presence of adventitious agents in vaccines manufactured in primary cell cultures and the associated need for extensive, expensive biosafety testing of each vaccine batch manufactured, there is a strong stimulus for the vaccine industry to change to continuous cell lines. Once a continuous cell line has been characterized the need for testing for adventitious agents of the production batches is minimal.

However, switch from primary to continuous cell culture for production of Vaccinia and Vaccinia recombinant vaccines is expected to impose stricter safety and regulatory requirements. In fact, the regulatory authorities have proposed new requirements for levels of DNA contaminants in vaccines manufactured using continuous cell lines (See Draft FDA guideline), which may be as low as 10 ng host-cell DNA/dose. To achieve such low level of host cell contaminants, new and improved methods for purification are needed.

It appears that vaccinia virions are able to bind to heparin through the surface protein A27L (Chung et al. 1998, J. Virol. 72, 1577-1585). At least three surface proteins A27L (Chung et al., J. Virol. 72(2):1577-1585, 1998; Ho et al., Journal of Molecular Biology 349(5):1060-1071, 2005; Hsiao et al., J. Virol. 72(10):8374-8379, 1998) D8L (Hsiao et al., J. Virol. 73(10):8750-8761, 1999), and H3L (Lin et al., J. Virol. 74(7): 3353-3365, 2000) of the most abundant infectious form of the Vaccinia virus have been reported to bind to glycosaminoglycans.

It has further been suggested that affinity chromatography (Zahn, A and Allain, J.-P. 2005, J. Gen. Virol. 86, 677-685) may be used as basis for purification of certain virus preparations. There are several examples for the application of ion exchange and affinity membrane adsorbers (MA) for the purification of virus particles like adenoviral vectors (Peixoto et al., Biotechnology Progress 24(6):1290-1296, 2008; Sellick, BioPharm International 19(1):31-32, 34, 2006), Aedes aegyptidensonucleosis virus (Enden et al., J Theor Biol 237 (3):257-264, 2005), baculovirus (Wu et al., Hum. Gene Ther. 18(7):665-672, 2007), and influenza virus (Kalbfuss et al., Journal of Membrane Science 299(1-2):251-260, 2007; Opitz et al., Biotechnol. and Bioeng. 103(6):1144-1154, 2009; and Opitz et al., Journal of Biotechnology 131(3):309-317, 2007).

For efficient purification of vaccinia virus and recombinant vaccinia virus-based vaccines, some significant challenges need to be overcome. Vaccinia virions are far too large to be effectively loaded onto commercially available heparin columns, e.g., the Hi-Trap heparin column from Amersham Biosciences used by others (Zahn, A and Allain, J.-P. 2005, J. Gen. Virol. 86, 677-685) for lab-scale purification of Hepatitis C and B viruses. The Vaccinia virion volume is approximately 125 times larger than Hepatitis virion. (The diameter of the Vaccinia virus is, thus, appr. 250 nm as compared with the hepatitis C and B virions diameter being appr. 50 nm). Thus, available matrices as, e.g., used in the column-based approach may not allow for adequate entrance of virions into the matrix, loading of sufficient amounts of virus particles or sufficiently rapid flow through the column to meet the needs for industrial scale purification. Zahn and Allain worked with virus load up to $1\times10^6$ in up to 1.0 ml volume. For pilot-scale purification to achieve sufficient material for early clinical trials virus loading capacity higher than $1\times10^{11}$, preferably up $1\times10^{13}$, in volumes higher than 5 L, preferably up to 50 L, is needed. For industrial purification of Vaccinia virus loading capacity higher than $1\times10^{13}$, preferably higher than $1\times10^{14}$ in volumes higher than 300 L, preferably higher than 600 L, is needed.

The large size of the Vaccinia virus may prevent effective steric access between the specific surface proteins of the virions and the ligand immobilized to the matrix. Currently described lab-scale methods of use for purification of small virus particles may therefore not be industrially applicable to purification of Vaccinia virus.

Due to the high number of functional surface molecules interacting with the ligand used for binding of the Vaccinia virus particles, elution of bound Vaccinia virus may require more harsh and therefore potentially denaturing conditions to elute and recover the Vaccinia virus particles in a biologically effective form in high yields. The matrix, the ligand design, the method of ligand immobilization, and the ligand density may therefore require careful design to mediate an effective binding of the Vaccinia virus and to permit an effective elution of biologically active Vaccinia virus particles.

Vaccinia virions are too large to be sterile filtered. The method used in this invention has therefore been developed by to be applicable for an aseptic industrial-scale manufacturing process in a way ensuring full compliance with regulatory requirements regarding sterility of vaccines. In line with the above and for the purpose of this invention, the column substituted with the ligand should be applicable for sterilization-in-place or should be available as a pre-sterilized unit.

The introduction of cell culture-derived smallpox vaccines required an adaptation of the original downstream processing schemes. Current smallpox vaccines like e.g. ACAM2000 are purified mainly after cell disruption by centrifugation and filtration methods (Abdalrhman et al., Vaccine 24(19):4152-4160, 2006; Greenberg and Kennedy, Expert Opinion on Investigational Drugs 17(4):555-564, 2008; and Monath et al., International Journal of Infectious Diseases 8(Supplement 2):31-44, 2004). The disadvantage of these methods is the limited depletion of contaminants like host cell DNA and proteins. In order to comply with regulatory expectations for current human smallpox vaccines based on continuous cell lines a nuclease treatment for host cell DNA depletion is often included in these processes (Greenberg and Kennedy, 2008; and Monath et al. 2004).

Examples of glycosaminoglycans in affinity chromatography applications are heparin and heparan sulfate. These are highly charged, linear and sulfated polysaccharides composed of repeating disaccharide units containing an uronic acid (glucuronic or iduronic acid) and an N-sulfated or N-acetylated glucosamine (Ampofo et al., Analytical Biochemistry 199(2):249-255, 1991; Nugent, Proceedings of the National Academy of Sciences of the United States of America 97(19):10301-10303, 2000; Rabenstein, Nat. Prod. Rep. 19:312-331, 2002).

Cellufine® sulfate and sulfated cellulose membranes are sulfated glucose polymers. Several studies reported antiviral activities of sulfated cellulose and sulfated dextran/dextrines (Baba et al., Antimicrob. Agents Chemother. 32(11):1742-1745, 1988; Chattopadhyay et al., International Journal of Biological Macromolecules 43(4):346-351, 2008; Mitsuya et al., Science 240(4852):646-649, 1988; Piret et al., J. Clin. Microbiol. 38(1):110-119, 2000), as well as the binding of virus particles to Cellufine® sulfate (O'Neil et al., Bio/Technology 11:173-178, 1993; Opitz et al., Biotechnol. and Bioeng. 103(6):1144-1154, 2009). The precise interaction between these viruses and sulfated cellulose is currently not fully understood.

To achieve a bio-specific purification of Vaccinia virus particles with high biological activity, there is a need in the art for development of industrially usable ligands identical to or very similar to the presumed native ligand for Vaccinia target cell entry. Thus, use of a ligand displaying highly specific and highly effective binding to the Vaccinia virus would be advantageous as it would improve purification by its ability to specifically sort out biologically active Vaccinia virus particles thereby increasing the purity, viability, and functionality of the purified Vaccinia virus.

BRIEF SUMMARY OF THE INVENTION

The invention encompasses methods for purifying viruses. The application of adsorption chromatography to capture cell-derived Vaccinia virus particles after cell homogenization and cell debris clearance is described. The invention includes virus purification using ion exchange and pseudo-affinity chromatography, preferably based on heparin and sulfated cellulose.

The ability of different ion exchange and pseudo-affinity membrane adsorbers to capture cell-derived Vaccinia virus after cell homogenization and clarification has been evaluated. In parallel, the overall performance of classical bead-based resin chromatography (Cellufine® sulfate and Toyopearl® AF-Heparin) was investigated. The two tested pseudo-affinity membrane adsorbers (i.e. sulfated cellulose and heparin) were superior over the applied ion exchange membrane adsorber in terms of virus yield and contaminant depletion. Furthermore, studies showed an increase in productivity resulting from the increased volume throughput of membrane adsorbers compared to classical bead-based column chromatography methods. Overall virus recovery was approximately 60% for both pseudo-affinity membrane adsorbers and the Cellufine® sulfate resin. Depletion of total protein ranged between 86% and 102% for all tested matrices. Remaining dsDNA in the product fraction varied between 24% and 7% for the pseudo-affinity chromatography materials. Cellufine® sulfate and the reinforced sulfated cellulose membrane adsorbers achieved the lowest dsDNA product contamination. Finally, by a combination of pseudo-affinity with anion exchange membrane adsorbers a further reduction of host cell DNA was achieved.

The invention encompasses methods for purifying biologically active Vaccinia viruses. In one embodiment, the method comprises loading a solid-phase matrix, to which a ligand is attached, with a biologically active Vaccinia virus contained in a liquid-phase culture, washing the matrix; and eluting the biologically active Vaccinia virus. Preferably, the matrix with attached ligand is a sulfated cellulose. In one embodiment, the solid-phase matrix comprises or is a membrane. In a preferred embodiment, the solid-phase matrix comprises or is a sulfated reinforced cellulose membrane.

In one embodiment, the method is an industrial-scale process. In one embodiment, the method is aseptic.

In a preferred embodiment, the eluted Vaccinia virus contains less than 10 ng host-cell DNA per $10^8$ virus particles.

In a preferred embodiment, the Vaccinia virus is a recombinant Vaccinia virus. In a particularly preferred embodiment, the Vaccinia virus is MVA or recombinant MVA.

In one embodiment, the matrix comprises a pore size of greater than 0.25 µm.

In one embodiment, contaminants are removed from the Vaccinia virus in the liquid-phase culture.

In one embodiment, the Vaccinia virus is eluted with sodium chloride (NaCl). In a preferred embodiment, the Vaccinia virus is eluted by an increasing NaCl concentration gradient ranging from 0.15 M to 2.0 M. Preferably, the Vaccinia virus is eluted with 2.0 M NaCl.

In one embodiment, a purification step by ion-exchange is included. In a preferred embodiment, the purification step by ion-exchange comprises a membrane.

In a preferred embodiment, the method reduces the amount of dsDNA in the eluted virus to less than 5% of input. In a particularly preferred embodiment, the method reduces the amount of dsDNA in the eluted virus to less than 0.1% of input.

In a preferred embodiment, the pH value of the virus preparation is adjusted to a pH ranging from 4.0-11.0.

In one embodiment, the eluted Vaccinia virus is administered to an animal, preferably a human.

Pierce® BCA protein assay) during the capturing of CEF cell-derived MVA-BN® using anion exchange MA Q75-MA and D75-MA (15 layers, d=25 mm, A=75 cm2), 3 serially connected cation exchangers C75-MA (3×15 layers, d=25 mm, A=225 cm2), 3 serially connected heparin-MA (3×15 layers, d=25 mm, A=225 cm2), SC-MA (15 layers, d=25 mm, A=75 cm2) and bead-based resin Cellufine® sulfate (3 ml fixed bed, Tricorn 5/150 column). Adsorption buffer: 100 mM citric acid, pH 7.2; elution buffer: 100 mM citric acid, 2 M NaCl, pH 7.2). The number of experiments is indicated in brackets in FIG. 1A; error bars: mean and standard deviation of each test series.

Figure 2:
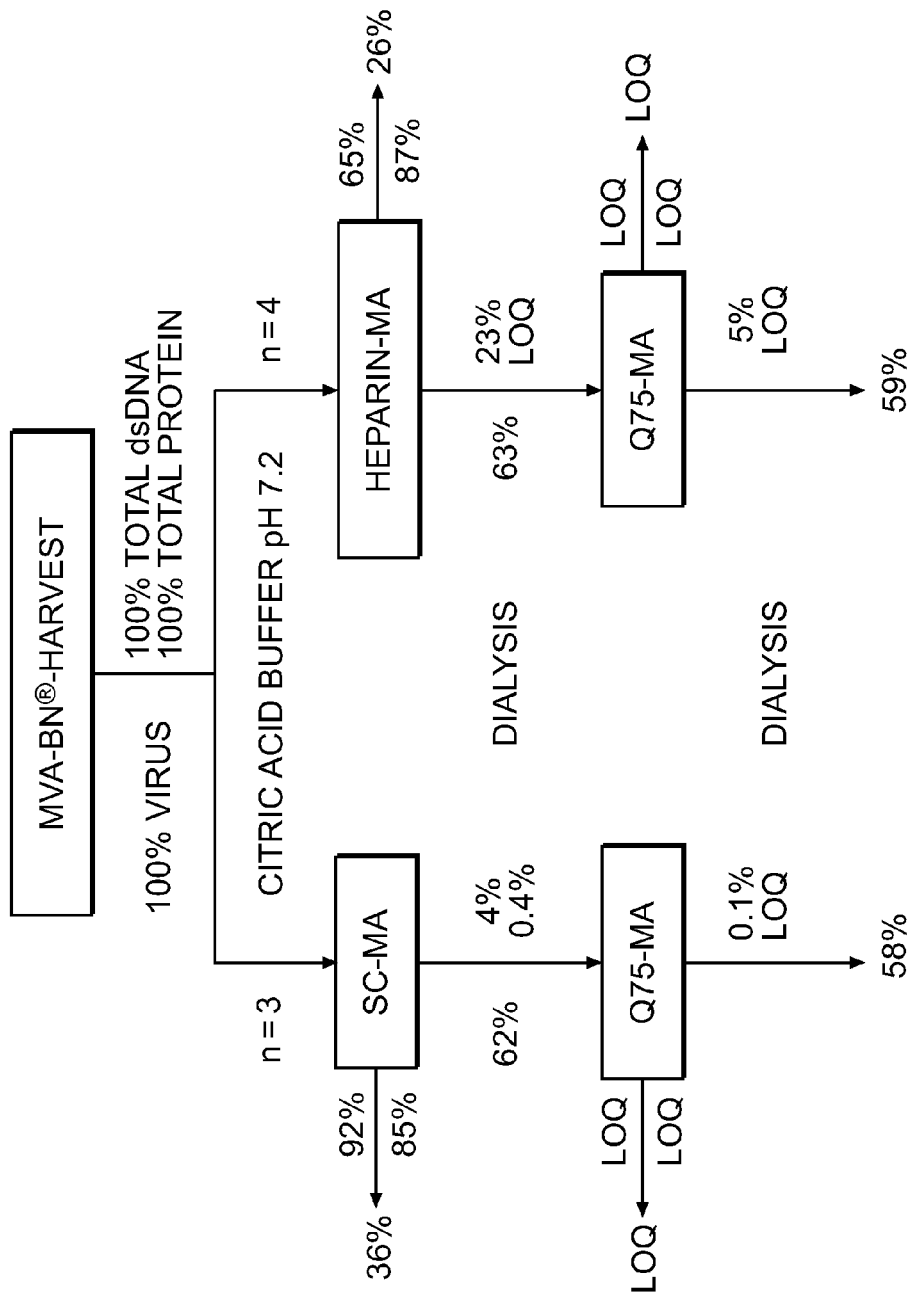

FIG. 2 depict the purification of MVA-BN® by a combination of a SC-MA (15 layers, d=25 mm, A=75 cm2) or heparin-MA (3×15 layers, d=25 mm, A=225 cm2) with an anion exchange MA Q75-MA (15 layers, d=25 mm, A=75 cm2). The equilibration buffer was for all cases 100 mM citric acid pH 7.2 and the elution buffer 100 mM citric acid+2 M NaCl pH 7.2. The flow rates for the adsorption process for the pseudo-affinity MA was 10 ml/min and the flow rate for desorption 0.5 ml/min. The adsorption and desorption flow rate of the Q75-MA was 0.5 ml/min. The relative virus content (green) was monitored by an ELISA; relative amounts of total protein (blue) and dsDNA (red) were quantified by the Pierce® BCA protein assay and the Quant iT™ PicoGreen® assay, respectively. ELISA and total protein analysis of individual samples were conducted in triplicates and the dsDNA measurements in duplicates; (n) indicates the number of chromatographic experiments.

DETAILED DESCRIPTION OF THE INVENTION

In particular, the present invention is directed to a method for the purification of biologically active Vaccinia virus comprising:

a. loading a solid-phase matrix, to which a ligand is attached, with a Vaccinia virus contained in a liquid-phase culture;

b. washing the matrix, and c. eluting the virus.

The ligand is a substance that, on the one hand, can be attached to the solid-phase matrix, e.g., by binding or coupling thereto and that, on the other hand, is able to form a reversible complex with the Vaccinia virus. Thus, by interacting with the virus, the virus is reversibly retained. The ligand can be a biological molecule as, for example, a peptide and/or a lectin and/or an antibody and/or, preferably, a carbohydrate. The ligand may also comprise or consist of sulfate. In a further embodiment, the ligand comprises one or more negatively charged sulfate groups. Furthermore, the ligand can also be a hydrophobic molecule as, for example, an aromatic phenyl group. The ligand can be attached to the matrix directly, e.g, by direct binding, or can be attached to the matrix indirectly though another molecule, e.g. by coupling through a linker or spacer.

The solid-phase matrix can be a gel, bead, well, membrane, column, etc. In a preferred embodiment of the invention, the solid-phase comprises or is a membrane, in particular a cellulose membrane. However, a broad range of other polymers modified with specific groups capable to bind the virus can be used. Preferred are hydrophilic polymers. Examples are cellulose derivatives (cellulose esters and mixtures thereof, cellulose hydrate, cellulose acetate, cellulose nitrate); agarose and its derivatives; other polysaccachrides like chitin and chitosan; polyolefines (polypropylene); polysulfone; ployethersulfone; polystyrene; aromatic and aliphatic polyamides; polysulfonamides; halogenated polymers (polyvinylchloride, polyvinylfluoride, polyvinylidenfluoride); polyesters; homo- and copolymers of acrylnitrile.

The method and further embodiments of the invention can overcome the limitations of currently known methods preventing industrial-scale, effective purification of Vaccinia virus particles with high biological activity and purity. The method is superior in terms of yield, process time, purity, recovery of biologically active Vaccinia virus particles and costs to existing pilot-scale methods for purification of Vaccinia virus particles, which are primarily based on sucrose-cushion centrifugation and/or diafiltration or non-specific ion-exchange chromatography. It is also superior in terms of yield, process time, purity, recovery of biologically active Vaccinia virus particles, and costs to the only existing large-scale method for purification of Vaccinia virus particles, which is based on ultrafiltration, enzymatic DNA degradation, and diafiltration.

According to the present invention, Vaccinia virus can be purified under aseptic conditions to obtain a biologically active, stable, and highly pure virus preparation in high yield. The Vaccinia viruses can be native or recombinant.

The present invention provides an improved method for aseptic purification of Vaccinia viruses in lab-, pilot-, and, preferably, in industrial-scale, leading to a biologically active, stable and highly pure virus preparation in high yield.

This invention provides a more time-effective and cost-effective process for purification of Vaccinia viruses and recombinant Vaccinia viruses, Modified Vaccinia virus Ankara (MVA) and recombinant MVA, MVA-BN® and recombinant MVA-BN®, leading to a biologically active, stable and highly pure virus preparation in high yield.

In another embodiment, this invention provides virus preparations produced by the method of the invention.

Use of the eluted Vaccinia virus or recombinant Vaccinia virus, or Modified Vaccinia virus Ankara (MVA) or recombinant MVA or MVA-BN® or recombinant MVA-BN®, all preferably obtained by the method according to the present invention, for the preparation of a pharmaceutical composition, in particular a vaccine, is also an embodiment of the invention. The virus and/or pharmaceutical preparation is preferably used for the treatment and/or the prevention of cancer and/or of an infectious disease.

A method for inducing an immune response or for the vaccination of an animal, specifically of a mammal, including a human, in need thereof, characterized by the administration of a Vaccinia virus or recombinant Vaccinia virus, or Modified Vaccinia virus Ankara (MVA) or recombinant MVA or MVA-BN® or recombinant MVA-BN® vaccine prepared by a process comprising a purification step as described above is a further embodiment of the invention.

As used herein, an "attenuated virus" is a strain of a virus whose pathogenicity has been reduced compared to its precursor, for example by serial passaging and/or by plaque purification on certain cell lines, or by other means, so that it has become less virulent because it does not replicate, or exhibits very little replication, but is still capable of initiating and stimulating a strong immune response equal to that of the natural virus or stronger, without producing the specific disease.

According to a further preferred embodiment of the present invention, glucosamine glycan (GAG), in particular heparan sulfate or heparin, or a GAG-like substance is used as ligand.

As used herein, "glycosaminoglycans" (GAGs) are long un-branched polysaccharides consisting of a repeating disaccharide unit. Some GAGs are located on the cell surface where they regulate a variety of biological activities such as developmental processes, blood coagulation, tumor metastasis, and virus infection.

As used herein, "GAG-like agents" are defined as any molecule which is similar to the known GAGs, but can be modified, for example, by the addition of extra sulfate groups (e.g. over-sulfated heparin). "GAG-like ligands" can be synthetic or naturally occurring substances. Additionally, the term "GAG-like ligands" also covers substances mimicking the properties of GAGs as ligands in ligand-solid-phase complexes. One example for a "GAG-like ligand" mimicking GAG, specifically heparin, as ligand is Sulfate attached to Reinforced Cellulose as solid-phase, thus forming Sulfated Reinforced Cellulose (SRC) as ligand-solid-phase complex. The use of SRC complex is also a preferred embodiment of the present invention. Stabilized Reinforced Cellulose membranes can be obtained, for example, from Sartorius AG.

As used herein, "Bulk Drug Substance" refers to the purified virus preparation just prior to the step of formulation, fill and finish into the final vaccine.

As used herein, "Biological activity" is defined as Vaccinia virus virions that are either 1) infectious in at least one cell type, e.g. CEFs, 2) immunogenic in humans, or 3) both infectious and immunogenic. A "biologically active" Vaccinia virus is one that is either infectious in at least one cell type, e.g. CEFs, or immunogenic in humans, or both. In a preferred embodiment, the Vaccinia virus is infectious in CEFs and is immunogenic in humans.

As used herein, "contaminants" cover any unwanted substances which may originate from the host cells used for virus growth (e.g. host cell DNA or protein) or from any additives used during the manufacturing process including upstream (e.g. gentamicin) and downstream (e.g. Benzonase).

As used herein, "continuous cell culture (or immortalized cell culture)" describes cells that have been propagated in culture since the establishment of a primary culture, and they are able to grow and survive beyond the natural limit of senescence. Such surviving cells are considered as immortal. The term immortalized cells were first applied for cancer cells which were able to avoid apoptosis by expressing a telomere-lengthening enzyme. Continuous or immortalized cell lines can be created, e.g., by induction of oncogenes or by loss of tumor suppressor genes.

As used herein, "heparan sulfate" is a member of the glycosaminoglycan family of carbohydrates. Heparan sulfate is very closely related in structure to heparin, and they both consist of repeating disaccharide units which are variably sulfated. The most common disaccharide unit in heparan sulfate consists of a glucuronic linked to N-acetyl glucosamine, which typically makes up approx. 50% of the total disaccharide units.

As used herein, "heparin" is a member of the glycosaminoglycan family of carbohydrates. Heparin is very closely related in structure to heparan sulfate, and they both consist of repeating disaccharide units which are variably sulfated. In heparin, the most common disaccharide unit consists of a sulfated iduronic acid linked to a sulfated glucopyranosyl. To differentiate heparin from heparan sulfate, it has been suggested that in order to qualify a GAG as heparin, the content of N-sulfate groups should largely exceed that of N-acetyl groups and the concentration of O-sulfate groups should exceed those of N-sulfate (Gallagher et al. 1985, Biochem. J. 230: 665-674).

As used herein, "industrial scale" or large-scale for the manufacturing of Vaccinia virus or recombinant Vaccinia virus-based vaccines comprises methods capable of providing a minimum of 50,000 doses of $1.0\times10^8$ virus particles (total minimum $5.0\times10^{12}$ virus particles) per batch (production run). Preferably, more than 100,000 doses of $1.0\times10^8$ virus particles (total minimum $1.0\times10^{13}$ virus particles) per batch (production run) are provided.

As used herein, "lab-scale" comprises virus preparation methods of providing less than 5,000 doses of $1.0\times10^8$ virus particles (total less than $5.0\times10^{11}$ virus particles) per batch (production run).

As used herein, "pilot-scale" comprises virus preparation methods of providing more than 5,000 doses of $1.0\times10^8$ virus particles (total more than $5.0\times10^{11}$ virus particles), but less than 50,000 doses of $1.0\times10^8$ virus particles (total minimum $5.0\times10^{12}$ virus particles) per batch (production run).

As used herein, "Primary cell culture", refers to the stage where the cells have been isolated from the relevant tissue (e.g. from specific pathogen free (SPF) hens eggs), but before the first sub-culture. This means that the cells have not been grown or divided any further from the original origin.

As used herein, "Purity" of the Vaccinia virus preparation or vaccine is investigated in relation to the content of the impurities DNA, protein, Benzonase, and gentamicin. The purity is expressed as specific impurity, which is the amount of each impurity per dose (e.g. ng DNA/dose).

As used herein, "purification" of a Vaccinia virus preparation refers to the removal or measurable reduction in the level of some contaminant in a Vaccinia virus preparation.

As used herein, "Recombinant Vaccinia virus" is a virus, where a piece of foreign genetic material (from e.g. HIV virus) has been inserted into the viral genome. Thereby, both the Vaccinia virus genes and any inserted genes will be expressed during infection of the Vaccinia virus in the host cell.

As used herein, "Stability" means a measure of how the quality of the virus preparation (Bulk Drug Substance (BDS) or Final Drug Product (FDP)) varies with time under the influence of a variety of environmental factors such as temperature, humidity and lights, and establishes a retest period for the BDS or a shelf-life for the FDP at recommended storage conditions (Guidance for industry Q1A (R2).

As used herein, a "Virus preparation" is a suspension containing virus. The suspension could be from any of the following steps in a manufacturing process: after virus growth, after virus harvest, after virus purification (typically the BDS), after formulation, or the final vaccine (FDP).

As used herein "vaccinia virus forms" refer to the three different types of virions produced by infected target cells: Mature virions (MV), wrapped virions (WV), and extra-cellular virions (EV) (Moss, B. 2006, Virology, 344:48-54). The EV form comprises the two forms previously known as cell-associated enveloped virus (CEV), and extra-cellular enveloped virus (EEV) (Smith, G. L. 2002, J. Gen. Virol. 83: 2915-2931).

The MV and EV forms are morphologically different since the EV form contains an additional lipoprotein envelope. Furthermore, these two forms contain different surface proteins (see Table 1), which are involved in the infection of the target cells by interaction with surface molecules on the target cell, such as glycosaminglycans (GAGs) (Carter, G. C. et al. 2005, J. Gen. Virol. 86: 12791290). The invention involves use of the purification of all forms of Vaccinia Virus.

The different forms of Vaccinia virions contain different surface proteins, which are involved in the infection of the target cells by interaction with surface molecules on the target cell, such as glycosaminglycans (GAGs) (Carter, G. C. et al. 2005, J. Gen. Virol. 86: 1279-1290). These surface proteins will as mentioned supra be referred to as receptors. On the MV form, a surface protein named p14 or A27L (the latter term will be used in this application) is involved in the initial attachment of the virions to the target cell. A27L binds to GAG structures on the target cell prior to entry into the cell (Chung C. et al. 1998, J. Virol. 72: 1577-1585), (Hsiao J. C. et al. 1998 J. Virol. 72: 8374-8379), (Vazquez M. et al. 1999, J. Virol. 73: 9098-9109) (Carter G. C. et al. 2005, J. Gen. Virol. 86: 1279-1290). The natural ligand for A27L is presumed to be the GAG known as heparan sulfate (HS). Heparan Sulfate belongs to a group of molecules known as glycosaminglycans (GAGs). GAGs are found ubiquitously on cell surfaces. (Taylor and Drickamer 2006, Introduction to Glycobiology, $2^{nd}$ edition, Oxford University Press). GAGs are negatively charged molecules containing sulfate groups. The A27L protein is located on the surface of the virions and is anchored to the membrane by interaction with the A17L protein (Rodriguez D. et al. 1993, J. Virol. 67: 3435-3440) (Vazquez M. et al. 1998, J. Virol. 72: 10126-10137). Therefore, the interaction between A27L and Al17L can be kept intact during isolation in order to retain full biological activity of the virions. The specific nature of the protein-protein interaction between A17L and A27L has not been fully elucidated, but it has been suggested that a presumed "Leucine-zipper" region in the A27L is involved in the interaction with A17L (Vazquez M. et al. 19981, J. Virol. 72: 10126-10137).

The invention encompasses the use of the affinity interaction between the A27L surface protein on the MV form and glucosaminglycans, in particular Heparan Sulfate, for purification of the MV form of Vaccinia Virus.

The term "ligand", thus, refers both to a receptor on a target cell and to the specific binding structure attached to a solid-phase matrix used for purification of Vaccinia.

The same principle as described above can be applied to interactions between other target cell surface structures and other Vaccinia surface proteins of the MV form participating in the Vaccinia virus' recognition of, attachment to, entry into and/or fusion with the target cell (see Table 1). Other WV and EV surface proteins are summarized in Table 1. The entire A27L protein, or fragments thereof containing the binding region for the GAG ligand can be used as agents to elute Vaccinia viruses-GAG complexes from a solid-phase column of the invention. Fragments can be readily generated by routine molecular techniques and screened for their ability to dissociate Vaccinia viruses-GAG complexes using routine techniques known in the art, such as by measuring eluted, biologically active virus.

The presumed native GAG-ligand for the MV form of Vaccinia is Heparan Sulfate (HS) and can be one of the suitable ligands. The invention also comprises use of "non-native" ligands for purification of Vaccinia virus. Such non-native ligands are compounds with a high degree of structural and/or conformational similarity to native ligands. As an example, Heparin, which is a close analogue to the native ligand for A27L, HS, can be used for affinity-purification of MV form by interaction with the A27L surface protein, see further below. Heparin has been shown to partially inhibit the binding between target cells and Vaccinia virus and can therefore also be used for affinity purification of the MV form of Vaccinia. Other GAG-ligands and GAG-like ligands can also be used.

In one embodiment of the invention, Heparan Sulfate, used for affinity purification of the MV form of Vaccinia, binds A27L on biologically active Vaccinia viruses, but does not bind inactive Vaccinia viruses or Vaccinia virus fragments.

The ligand makes possible the elution of the bound Vaccinia virus under such mild conditions that the Vaccinia virus fully retain their biologically activity. This means that the structure of A27L and the interaction between A27L and A17L can be kept intact.

The binding and elution characteristics for the GAG-ligand substituted matrix depend not only on the individual characteristics of the matrix and ligand, but also on the interplay between the two.

By modifying e.g. the ligand density or by attaching, e.g. binding or coupling of, the ligand to the matrix by "arms" or "spacers" of different length and chemical characteristics (hydrophobicity, hydrophilicity) the binding strength between the target GAG-ligand structure and the A27L surface protein on the Vaccinia virus can be altered, which can be used to e.g. enhance the capture or ease the elution.

To enhance the purification method, the matrix in the form of a chromatography gel or membrane to be used for the purification preferably:

Has a high pore size (to make as many ligands as possible accessible to the Vaccinia virus)
Has a rigid structure to allow for fast flow rates
Is available in a form permitting direct or indirect attachment, e.g. by binding or coupling, of ligands
Is applicable for sterilization in place or available as a pre-sterilized unit, e.g. by using radiation.

In one embodiment, the solid phase matrix is a gel or membrane with a pore size of 0.25 µm, preferably of more than 0.25 µm, more preferably of 1.0-3.0 µm demonstrating a linear flow rate under actual purification conditions of 10 cm/min, preferably 20 cm/min. The pore size of the matrix can be 0.25-0.5 µm, 0.5-0.75 µm, 0.75-1.0 µm, 1.0-2.0 µm, 2.0-3.0 µm, or greater than 3.0 µm.

In one embodiment, with the solid phase matrix containing a heparan sulfate as an immobilized ligand, the virus harvest from the upstream virus growth process is loaded in a crude (unpurified) form with a flow rate of 10 cm/min, preferably 20 cm/min at a virus concentration of $10^6$ virions per mL in pilot scale and $10^7$ virions per mL in industrial scale.

In one embodiment, there are three steps in the purification process of the invention, which are common for most affinity chromatography processes:
1) Loading of Vaccinia virus or Vaccinia recombinant virus onto the solid phase;
2) Washing of the solid phase to remove contaminants; and
3) Elution of the Vaccinia virus or recombinant virus to be isolated.

Step 1. Loading of Vaccinia Virus or Recombinant Virus onto a Solid-phase Matrix Loading to the solid phase with, e.g., Heparane Sulphate or another GAG or GAG-like structure attached as ligand, can be performed by a batch-, column- or membrane approach.

The membrane approach can have some benefits, specifically for large bio-molecules, in particular for large viruses like Vaccinia viruses: For example, large pore sizes and the availability of the ligand on the surface of the membrane allow high binding capacities of even large viral particles. The membrane approach is, thus, a preferred embodiment of the present invention.

In all embodiments mentioned above, the Vaccinia virus or recombinant virus to be isolated is present in a liquid phase. When the Vaccinia virus or recombinant virus gets close to the GAG or GAG-like ligand the Vaccinia virus will bind specifically to or be "captured by" the GAG-ligand, thereby the Vaccinia virus or recombinant Vaccinia virus can be temporarily immobilized on the solid phase, while the contaminants will remain in the liquid phase.

By appropriate selection of the ligand type, ligand density and ligand steric configuration, the binding parameters of Vaccinia virus via A27L surface protein to the column can be altered, thereby providing means for optimization of the purification parameters.

Step 2. Washing of the Solid Phase to Remove Contaminants

When the binding of the biologically active Vaccinia viruses or recombinant viruses to the ligand has proceeded sufficiently, the host cell contaminants (in particular host cell DNA and proteins) that remain in the liquid phase can be removed by washing the solid phase, to which the Vaccinia virus is bound, with an appropriate washing medium.

Step 3. Eluting the Vaccinia Virus or Recombinant Virus by Specific or Non-specific Agents The biologically active Vaccinia viruses or recombinant viruses can be eluted. The elution of the captured Vaccinia virus can be performed, for example, by:

Agents specifically disrupting the specific interaction between, e.g., the GAG-ligand and the A27L surface protein on the Vaccinia virus (to be called specific agents), or by Agents non-specifically disrupting the electrostatic interaction between, e.g., the negatively charged GAG-ligand and the positively charged A27L surface protein (to be called non-specific agents).

According to further embodiments of the present invention, the Vaccinia virus is eluted with GAG or a GAG-like ligand or part thereof, with the GAG-binding domain of A27L or part thereof, and/or with an O-glycoside-binding cleaving enzyme.

Elution of the virus is, further, preferably performed with sodium chloride, more preferably by an increasing NaCl concentration gradient ranging from 0.15 M to 2.0 M.

Pre-treatment

Prior to loading on the solid phase, a pre-treatment of the virus suspension can be performed, specifically in order to remove contaminants from the Vaccinia virus in the liquid-phase culture.

Pre-treatment can be one or more of the following steps either alone or in combination:
1) Homogenization of the host cells
   Ultrasound treatment
   Freeze/thaw
   Hypo-osmotic lysis
   High-pressure treatment
2) Removal of cell debris
   Centrifugation
   Filtration
3) Removal/reduction of host cell DNA
   Benzonase treatment
   Cationic exchange
   Selective precipitation by cationic detergents According to a further embodiment of the invention, the pH value of the viral suspension is decreased just prior to loading in order to improve the binding of the virus particle to the ligand. The pH value of the viral suspension can be decreased from appr. pH 7.0-8.0 to 4.0-6.9, in particular to pH 4.0, 4.2, 4.4, 4.5, 4.6, 4.8, 5.0, 5.2, 5.4, 5.5, 5.6, 5.8, 6.0, 6.2, 6.4, 6.5, 6.6, 6.8, 6.9. Preferably, the pH value is decreased from pH 7.0-8.0 to pH 5.8. Subsequently, just after loading and before elution, the pH value is again increased to pH 7.0-8.0, in particular to pH 7.0, 7.2, 7.4, 7.5, 7.6, 7.8, 8.0, preferably to pH 7.7, in order to improve the stability of the viral particles.

Post-treatment

Depending on the agent used for elution of the Vaccinia virus or recombinant virus, post-treatment can be performed to enhance the purity of the virus preparation. The post-treatment could be ultra/diafiltration for further removal of impurities and/or specific or non-specific agents used for elution. To obtain an efficient purification of the virus, it is also preferred to combine the purification according to the invention with one or more further purification steps, e.g., by ion-exchange(s). Ion-exchange(s) can, then, also be performed as post-treatment step(s).

In order to prevent aggregation of the purified virus suspension and, thus, to, inter alia, improve the detection of infectious particles, in particular by the TCID50 method, it can also be suitable to increase the pH value after elution of the virus, in particular to a pH value of up to 9 or more, in particular to pH 7.5, 7.6, 7.8, 8.0, 8.2, 8.4, 8.5, 8.6, 8.8, 9.0, 9.2, 9.4, 9.5, 9.6, 9.8, 10.0, 10.2, 10.4, 10.5. Preferably, the pH value is increased from, in particular, pH 7.0, 7.2, 7.4, 7.5, 7.6, 7.8, 8.0, preferably pH 7.7, to pH 9.0.

According to a further embodiment of the present invention, the Vaccinia virus sample contains host-cell DNA in the range of 10-20 µg per dose ($1\times10^8$ TCID$_{50}$–$3.2\times10^8$ TCID$_{50}$), preferably 10 ng, more preferably less than 10 ng host-cell DNA per $10^8$ virus particles after performance of the purification steps according to the invention, i.e, after elution of the virus.

Preferably, the amount of host-cell DNA in a VV dose of $1\times10^8$ TCID$_{50}$ is 10-20 µg, 1-10 µg, 100 ng-1 µg, 10-100 ng, or 1-10 ng. The amount of dsDNA in a VV sample can be reduced by the purification method to less than 40%, 20%, 10%, 5%, 1%, 0.5%, or 0.1% of input.

Preferably, amount of protein in the purified VV is less than 250 µg/ml, 100 µg/ml, 50 µg/ml g, 20 µg/ml, 10 µg/ml, or 5 µg/ml.

The practice of the invention employs techniques in molecular biology, protein analysis, and microbiology, which are within the skilled practitioner of the art. Such techniques are explained fully in, for example, Ausubel et al. 1995, eds, Current Protocols in Molecular Biology, John Wiley & Sons, New York.

Modifications and variations of this invention will be apparent to those skilled in the art. The specific embodiments described herein are offered by the way of example only, and the invention is not to be construed as limited thereby.

In one embodiment, the invention provides a more time-effective and cost-effective process for purification of Vaccinia viruses and recombinant-modified Vaccinia viruses in higher yield, comprising one or more of the following steps:
  a. loading a solid-phase matrix with a liquid-phase virus preparation, wherein the solid-phase matrix comprises a ligand appropriate for interacting with the virus, e.g. by reversibly binding the virus
  b. washing of the matrix, and
  c. eluting the virus.

Additional aspects and advantages of the invention will be set forth in part in the description which follows, and in part will be obvious from the description, or may be learned by practice of the invention.

In a preferred embodiment, the method comprises the following steps:
  a. Loading a column, membrane, filter or similar solid-phase matrix comprising one or more appropriate virus-binding ligands with a liquid-phase virus preparation,
  b. Washing of the matrix with an appropriate solvent to remove contaminants, and
  c. Eluting the Vaccinia virus with an appropriate solvent to achieve a highly pure, biologically active, stable virus preparation.

In a further preferred embodiment, the method comprises the following steps:
  a. Loading a column, membrane, filter or similar solid-phase matrix comprising one or more appropriate glucosamine glycan (GAG) or GAG-like virus-binding ligands with a liquid-phase virus preparation b. Washing of the matrix with an appropriate solvent to remove contaminants, and c. Eluting the Vaccinia virus with a solvent resulting in an concentration gradient of a non-specific eluent such as NaCl, H+ or of specific eluent such as a GAG-like compound or and A27L peptide or peptide-fragment to achieve a highly pure, biologically active, stable virus preparation.

In one particularly preferred embodiment, the method is used for the purification of biologically active Vaccinia virus and comprises the following steps:

a. Loading a column, membrane, filter or similar solid-phase matrix substituted with a Heparin (HP) with a Vaccinia virus preparation dissolved in a neutral buffer (pH 6.5 to 8.5, preferably >=pH 7.5) with a physiological salt concentration (approximately 150 mM NaCl), b. Washing of the matrix with a sufficient amount of the loading buffer to ensure complete elution of all non-binding Vaccinia virus particles and non-binding contaminants, and c. Eluting the Vaccinia virus with an increasing concentration of NaCl, from 0.15 to 2.0 M NaCl, to initially remove contaminants with less affinity than the Vaccinia virus particles and to finally elute the biologically active Vaccinia virus particles.

In another particularly preferred embodiment, the method is used for the purification of biologically active Vaccinia virus and comprises the following steps:

a. Loading a column, membrane, filter or similar solid-phase matrix substituted with a Heparin (HP) with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M b. Washing of the matrix with a sufficient amount of the loading buffer e.g. PBS (0.01 M phosphate, 0.15 M NaCl, pH 7.5) to ensure complete elution of all non-binding Vaccinia virus particles and nonbinding contaminants, as measured by the return of the 280 nm absorbance signal to the pre-loading baseline, and c. Eluting the Vaccinia virus with an increasing concentration of NaCl in PBS, starting with 0.15 M and ending with 2.0 M NaCl.

In another particularly preferred embodiment, the method is used for the purification of biologically active Vaccinia virus and comprises the following steps:

a. Loading a column, membrane, filter or similar solid-phase matrix substituted with a Heparin (HP) with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M NaCl, pH 8.0, and HEPES-NaCl, e.g. 0.01 to 0.1 M HEPES, 0.15 M NaCl, pH 7.5, b. Washing (Wash 1) of the matrix with a sufficient amount of the loading buffer e.g. PBS (0.01 M phosphate, 0.15 M NaCl, pH 7.5) to ensure complete elution of all non-binding Vaccinia virus particles and non-binding contaminants, as measured by the return of the 280 nm absorbance signal to the pre-loading baseline, c. Washing (Wash 2) of the matrix with an additional washing buffer e.g. Glycine Buffered Saline (GBS) 0.02 M, 0.15 M NaCl, pH 9.0) to remove loosely bound contaminants, and d. Eluting the Vaccinia virus with an increasing concentration of NaCl in GBS 0.02 M pH 9.0, starting with 0.15 M and ending with 2.0 M NaCl.

In another particularly preferred embodiment, the method is used for the purification of biologically active Vaccinia virus and comprises the following steps:

a. Loading a column, membrane, filter or similar solid-phase matrix substituted with a Heparane Sulphate (HS) with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M b. Washing of the matrix with a sufficient amount of the loading buffer e.g. to ensure complete elution of all non-binding Vaccinia virus particles and non-binding contaminants, as measured by the return of the 280 nm absorbance signal to the pre-loading baseline, and c. Eluting the Vaccinia virus with an increasing concentration of Low Molecular Weight Heparin, 0.01 to 0.5 M, in PBS 0.1 M, NaCl 0.15 M, pH 7.5.

In another particularly preferred embodiment, the method is used for the purification of biologically active Vaccinia virus and comprises the following steps:

a. Loading a column, membrane, filter or similar solid-phase matrix substituted with a Heparane Sulphate (HS) with a Vaccinia virus preparation dissolved in Phosphate Buffered Saline (PBS), 0.02 M phosphate, 0.15 M NaCl, pH 7.5, b. Washing of the matrix with a sufficient amount of the loading buffer e.g. to ensure complete elution of all non-binding Vaccinia virus particles and non-binding contaminants, as measured by the return of the 280 nm absorbance signal to the pre-loading baseline, and c. Eluting the Vaccinia virus with an increasing concentration of an HS-derived oligosaccharide. The basic repeating disaccharide unit in HS-derived oligosaccharide is a,(31-→4-linked sequence of glucosamine and uronic acid. The glucosamine residues are either N-acetylated (GlcNAc) or N-sulphated (GlcNSO3-). Other monosaccharide residues e.g. iduronic acid and substitutions may occur, e.g. 2-0-sulphated iduronic acid. The oligosaccharide consists of 2 to 10 repeating disaccharide units. The oligosaccharide concentration used for elution of the Vaccinia virus particles runs from 0.01 M to 0.5 M in PBS, 0.02 M phosphate, 0.15 M NaCl, pH 7.5.

In another particularly preferred embodiment, the method is used for the purification of biologically active Vaccinia virus and comprises the following steps:

a. Loading a column, membrane, filter or similar solid-phase matrix substituted with a Heparane Sulphate (HS) with a Vaccinia virus preparation dissolved in Phosphate Buffered Saline (PBS), 0.02 M phosphate, 0.15 M NaCl, pH 7.5, b. Washing of the matrix with a sufficient amount of the loading buffer e.g. to ensure complete elution of all non-binding Vaccinia virus particles and non-binding contaminants, as measured by the return of the 280 nm absorbance signal to the pre-loading baseline, and c. Eluting the Vaccinia virus with an increasing concentration of an Vaccinia virus particles surface protein or a peptide or peptide-fragment derived hereof. The preferred surface protein is A27L, the preferred peptide is A27L, and the preferred A27L peptide-fragment is fragment containing 4-10 amino acid residues of the A27L peptide sequence responsible for the binding between A27L and the HS. The peptide concentration used for elution of the Vaccinia virus particles runs from 0.01 M to 0.5 M in PBS, 0.02 M phosphate, 0.15 M NaCl, pH 7.5.

In another particularly preferred embodiment, the method is used for the purification of biologically active Vaccinia virus and comprises the following steps:

a. Loading a column, membrane, filter or similar solid-phase matrix substituted with a Heparane Sulphate (HS) with a Vaccinia virus preparation dissolved in Phosphate Buffered Saline (PBS), 0.02 M phosphate, 0.15 M NaCl, pH 7.5,
b. Washing of the matrix with a sufficient amount of the loading buffer e.g. to ensure complete elution of all non-binding Vaccinia virus particles and non-binding contaminants, as measured by the return of the 280 nm absorbance signal to the pre-loading baseline, and
c. Eluting the Vaccinia virus with an enzyme capable of partially cleaving one or more glycoside linkages between the repeating disaccharide units, inside the repeating disaccharide unit or elsewhere in the HS molecule. Preferred enzymes are Heparin Lyase I, II and III. The elution is performed by saturation of the column with the enzyme solution. After an appropriate digestion time the unbound complex of Vaccinia virus particles and GAG-residues bound to the Vaccinia virus particles is eluted with PBS, 0.02 M phosphate, 0.15 M NaCl, pH 7.5. The Vaccinia virus particle-GAG-residue complex is dissociated with a mild NaCl solution e.g. PBS 0.02 M, 0.15 M NaCl, pH 7.5 and the GAG-residues are removed by diafiltration.

EXAMPLES

Affinity purifications are made applying either column chromatography with e.g. Toyopearls or membrane chromatography using e.g. a membrane (e.g. Sartobind MA 75 (Sartorius)) both of which are substituted with a GAG-ligand (e.g. Heparin or Heparan Sulfate) or a GAG-like ligand.

The below mentioned examples are all in lab-scale.

Example 1

Two ml of a highly concentrated and previously purified Vaccinia virus preparation with approximately $2\times10^9$ virus particles per ml were applied to a column with packed with Toyopearl AF-Heparin.

The column was washed with PBS 0.01 M, 0.15 M NaCl, pH 7.2. The A280 absorbance signal used for monitoring of Vaccinia virus particle and host cell protein concentrations returned to baseline (the pre-loading value) after 12 minutes. The washing continued for a total of 25 minutes.

The bound Vaccinia virus particles were eluted by a NaCl concentration gradient in PBS 0.01 M, pH 7.2. The concentration of NaCl was increased linearly from 0.15 M to 2.0 M. The elution started after approximately a total of 30 minutes (5 minutes after starting the gradient). The major peak was eluted 7 minutes later (at T=37 minutes). The peak contained a high concentration of Vaccinia virus particles as assessed by the Laser Scattering signal used for monitoring of Vaccinia virus particles. The elution was completed after approximately 25 minutes (T=55 minutes).

The eluate was analyzed by a Vaccinia Virus specific ELISA showing a virus recovery rate of appr. 70%-90%. Host cell protein was analysed by use of the BCA total protein assay showing appr. 10% of protein in the eluate. Host cell DNA was analysed by a total DNA assay showing an additional removal of DNA of appr. 40% in the wash and flow-through.

Example 2

Two ml of a highly concentrated and previously purified Vaccinia virus preparation with approximately $2\times10^9$ virus particles per ml was applied to a Sartobind MA75 Heparin membrane.

The membrane was washed with PBS 0.01 M, 0.15 M NaCl, pH 7.5. The A280 absorbance signal used for monitoring of Vaccinia virus particle and host cell protein concentrations returned to baseline (the pre-loading value) after 12 minutes. The washing continued for a total of 16 minutes.

The bound Vaccinia virus particles were eluted by a NaCl concentration gradient in PBS 0.01 M, pH 7.5. The concentration of NaCl was increased linearly from 0.15 M to 2.0 M. The elution started after approximately a total of 20 minutes (4 minutes after starting the gradient). The major peak was eluted 5 minutes later (at T=25 minutes). The peak contained a high concentration of Vaccinia virus particles as assessed by the Laser Scattering signal used for monitoring of Vaccinia virus particles.

The eluate was analyzed by a Vaccinia Virus specific ELISA showing a virus recovery rate of appr. 55%. Host cell protein was analyzed by use of the BCA total protein assay and revealed a protein recovery of appr. 5% in the eluate. Host cell DNA was analyzed by a total DNA assay and revealed appr. 10% DNA in the eluate.

Example 3

Two ml of a highly concentrated Vaccinia virus preparation with approximately $2\times10^9$ virus particles per ml are applied to a Sartobind MA75 Heparin membrane.

The membrane is washed with PBS 0.01 M, 0.15 M NaCl, pH 7.5. The A280 absorbance signal is used for monitoring of Vaccinia virus particle and the host cell protein concentrations until it returns to baseline (the pre-loading value). The washings are continued for a total of 20 minutes.

The bound Vaccinia virus particles are eluted by a pH concentration gradient in GBS 0.02 M, 0.15 M NaCl. The initial pH is 8.5, increasing to pH 10.5. The concentration of NaCl is increased linearly from 0.15 M to 2.0 M.

The eluate is analyzed by titration for viable (infectious) Vaccinia virus particles by a Tissue Culture cytopatic effect assay (TCID50), for total number of Vaccinia virus particles by a real-time qPCR for Vaccinia DNA, for host cell protein by use of the BCA total protein assay and for host cell DNA by use of a real-time qPCR. The recovery can be >60% and biological activity of the recovered Vaccinia virus can be >75%.

Example 4

Two ml of a highly concentrated Vaccinia virus preparation with approximately $2\times10^9$ virus particles per ml are applied to a Sartobind MA75 Heparin membrane.

The membrane is washed with PBS 0.01 M, 0.15 M NaCl, pH 7.5. The A280 absorbance signal is used for monitoring of Vaccinia virus particle and the host cell protein concentrations until it returns to baseline (the pre-loading value). The washings are continued for a total of 20 minutes.

The elution is performed with a concentration gradient of low-molecular weight heparin (LMW-HP) in PBS 0.1 M, 0.15 M NaCl, pH 7.5. The gradient is run from 0.01 to 0.5 M LMW-Heparin.

The eluate is analyzed by titration for viable (infectious) Vaccinia virus particles by a Tissue Culture cytopathic effect assay (TCID50), for total number of Vaccinia virus particles by a real-time qPCR for Vaccinia DNA, for host cell protein by use of the BCA total protein assay and for host cell DNA by use of a real-time qPCR. The recovery can be >70% and biological activity of the recovered Vaccinia virus can be >80%.

Example 5

Two ml of a highly concentrated Vaccinia virus preparation with approximately $2 \times 10^9$ virus particles per ml are applied to a Sartobind MA75 Heparin membrane.

The membrane is washed with PBS 0.01 M, 0.15 M NaCl, pH 7.5. The A280 absorbance signal is used for monitoring of Vaccinia virus particle and the host cell protein concentrations until it returns to baseline (the preloading value). The washings are continued for a total of 20 minutes.

The elution is performed with a concentration of a gradient of A27L peptide (A27LP) in PBS 0.1 M, 0.15 M NaCl, pH 7.5. The gradient is run from 0.01 to 0.5 M A27LP.

The eluate is analyzed by titration for viable (infectious) Vaccinia virus particles by a Tissue Culture cytopatic effect assay (TCID50), for total number of Vaccinia virus particles by a real-time qPCR for Vaccinia DNA, for host cell protein by use of the BCA total protein assay and for host cell DNA by use of a real-time qPCR. The recovery can be >70% and biological activity of the recovered Vaccinia virus can be >80%.

Example 6

Two ml of a highly concentrated Vaccinia virus preparation with approximately $2 \times 10^9$ virus particles per ml are applied to a Sartobind MA75 Heparin membrane.

The membrane is washed with PBS 0.01 M, 0.15 M NaCl, pH 7.5. The A280 absorbance signal is used for monitoring of Vaccinia virus particle and the host cell protein concentrations until it returns to baseline (the pre-loading value). The washings are continued for a total of 20 minutes.

The elution is performed with a glycoside linkage cleaving enzyme Heparin Lyase in PBS 0.1 M, 0.15 M NaCl, pH 7.5. The membrane is saturated with Heparin Lyase by running 2 volumes of Heparin Lyase through the column.

After allowing 60 minutes for enzymatic cleavage of the glycoside linkage, the unbound complexes of Vaccinia virus particles and heparin-residues bound to the Vaccinia virus particles are eluted with PBS, 0.02 M phosphate, 0.15 M NaCl, pH 7.5. The Vaccinia virus particle-GAG-residue complex is dissociated with PBS 0.02 M, 0.3 M NaCl, pH 7.5. The Heparin-residues are removed by diafiltration.

The eluate is analyzed by titration for viable (infectious) Vaccinia virus particles by a Tissue Culture cytopathic effect assay (TCID50), for total number of Vaccinia virus particles by a real-time qPCR for Vaccinia DNA, for host cell protein by use of the BCA total protein assay and for host cell DNA by use of a real-time qPCR. The recovery can be >70% and biological activity of the recovered Vaccinia virus can be >80%.

Example 7

Two ml of a highly concentrated and previously purified Vaccinia virus preparation with approximately $2 \times 10^9$ virus particles per ml were applied to a Sulfated Reinforced Cellulose membrane.

The membrane was washed with PBS 0.01 M, 0.15 M NaCl, pH 7.5. The A280 absorbance signal was used for monitoring of Vaccinia virus particle and the host cell protein concentrations until it returned to baseline (the pre-loading value). The washings were continued for a total of 25 minutes.

The bound Vaccinia virus particles were eluted by a NaCl concentration gradient in PBS 0.01 M, pH 7.5. The concentration of NaCl was increased linearly from 0.15 M to 2.0 M. The elution started after approximately a total of 30 minutes (5 minutes after starting the gradient). The major peak was eluted 5 minutes later (at T=35 minutes). The peak contained a high concentration of Vaccinia virus particles as assessed by the Laser Scattering signal used for monitoring of Vaccinia virus particles.

The eluate was analyzed by a Vaccinia Virus specific ELISA showing a virus recovery rate of approx 40%. Host-cell protein was analyzed by use of the BCA total protein assay and showed a protein recovery of approx 5% in the eluate. Host-cell DNA was analyzed by a total DNA assay and showed approx 5% DNA in the eluate.

Example 8

Production of Modified Vaccinia Ankara Virus Particles

MVA-BN® virus particles were produced in primary cultures of CEF cells under Good Manufacturing Practice conditions. The starting material for this study was provided after homogenization and clarification as a liquid frozen product, stored in aliquots at −20° C. or −80° C.

MVA-BN®-Quantification

Virus titers were determined in triplicates by a sandwich ELISA. The relative virus amounts were correlated to the initial $TCID_{50}$ value. As capturing antibody a rabbit anti-Vaccinia virus (Cat.# 220100717; Quartett Immunodiagnostika & Biotechnologie GmbH, Germany) was used. The detection antibody was a peroxidase conjugated polyclonal rabbit anti-Vaccinia virus antibody (Cat.# 8104; ViroStat, USA).

Total Protein Assay

Total protein concentrations were determined in triplicates by the Pierce® BCA protein assay reagent kit (Cat.# 23225; Pierce Biotechnology, USA) according to the manufacture's instructions. The assay was calibrated against albumin standards (BSA) (Cat.# 23209; Thermo Fisher Scientific Inc., USA) within the validated working range of 25 to 250 µg/ml (LOD: 8.3 µg/ml; LOQ: 25 µg/ml) using 100 mM citric acid and 250 mM NaCl buffer pH 7.2 for dilutions. All samples were adjusted to the same buffer conditions.

dsDNA-assay

The dsDNA measurements were done as described by Opitz et al. (Opitz et al., Vaccine 25(5):939-947, 2007) using the Quant-iT™ PicoGreen® dsDNA reagent from Molecular Probes, Inc. (Cat.# P7581, USA). The assay was calibrated against lambda DNA (Cat.# D1501, Promega Corporation, USA) within the validated working range of 4 to 1000 ng/ml (weighted regression; LOD: 0.66 ng/ml; LOQ: 2.36 ng/ml) using 100 mM citric acid buffer pH 7.2 for dilutions. The same buffer was used for sample preparation via dialysis (5000 kDa MWCO; Cat.# 131192, Spectrum Europe B.V., Netherlands) and sample dilutions. After incubation of standards and samples with the reagent, the fluorescent signal was measured at an emission and excitation wavelength of 535 nm and 485 nm, respectively (Mithras LB 940, Berthold Technologies GmbH & Co.KG, Germany). All samples were measured in duplicates.

Chromatography Materials

Pseudo-affinity membrane adsorbers—Heparin-MA (Sartorius Stedim Biotech GmbH, Germany) was based on reinforced stabilized cellulose with a pore size >3 μm and an adsorption area of 3×75 cm² by 3×15 layers. The housing material was polypropylene. Sulfated cellulose MA (SC-MA) with a diameter of 25 mm (pore size >3 μm, Sartorius Stedim Biotech GmbH, Germany) were prepared as described previously (Opitz et al., Biotechnol. and Bioeng. 103(6):1144-1154, 2009). The adsorption area was 75 cm² and 15 membranes were stacked in a stainless steel membrane holder (Cat.# 1980-002, GE Healthcare, Germany).

Ion exchange membrane adsorbers—Dynamic binding capacity studies and capturing experiments were conducted by four different ion exchange MA: A strong anion exchange MA (Sartobind Q75-MA; Cat.# Q75X; 75 cm², 15 layers), a weak anion exchange MA (Sartobind D75-MA; Cat.# D75X; 75 cm², 15 layers), a strong cation exchange MA (Sartobind S75-MA; Cat.# S75X; 75 cm², 15 layers) and a weak cation exchange MA (Sartobind 075-MA; Cat.# C75X; 75 cm², 15 layers). All ion exchange MA were from Sartorius Stedim Biotech GmbH, Germany.

Bead-based pseudo-affinity resins—Cellufine® sulfate (3 ml, Cat. #19845, Chisso Corporation, Japan), and Toyopearl AF-Heparin HC-650M (3 ml, Cat. # 20030, Tosoh Bioscience, Germany) were packed into a Tricorn 5/150 column (GE Healthcare, Germany).

Adsorption Chromatography

Chromatography was performed using an Akta Explorer system (GE Healthcare, Germany) at a flow rate of 0.5 ml/min (unless stated differently) and monitored by UV (280 nm) and light scattering (90°, Dawn EOS, Wyatt Technology Inc., USA) detection.

Dynamic binding capacity of the chromatography media was determined loading the clarified MVA-BN® virus sample (4.65×10⁷ $TCID_{50}$/ml) at a flow rate of 0.5 ml/min onto Sartobind S75-MA, C75-MA, Q75-MA, D75-MA, Heparin-MA and SC-MA. All applied MA had a surface area of 75 cm² and were composed of 15 layers. In parallel, the dynamic binding capacity was determined for the 3 ml Cellufine® sulfate and Toyopearl® AF-Heparin beads. The breakthrough was monitored via light scattering detector.

Figure 1A:
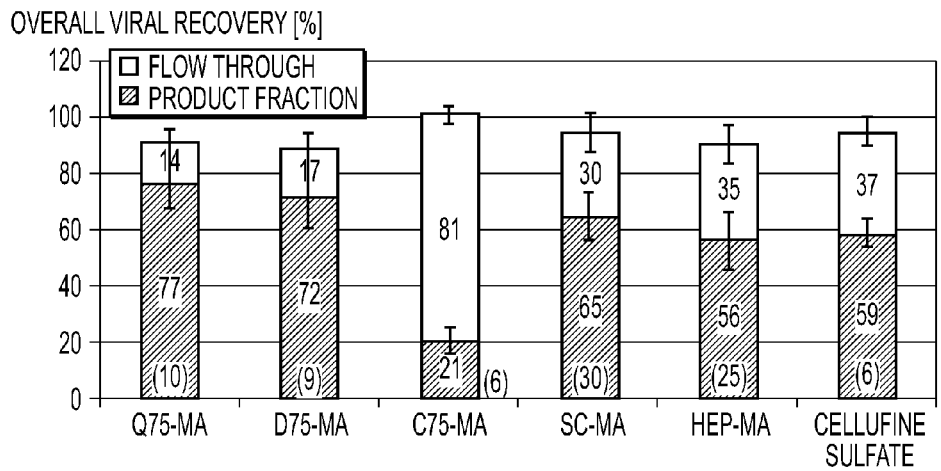
FIG. 1A-C depict the relative amounts of virus (A; ELISA), total dsDNA (B; PicoGreen®) and total protein (C.

Characterization of the chromatography materials was done with 4 ml of the clarified MVA-BN® virus sample, representing a dynamic binding capacity of approximately 49% for the C75-MA (3×75 cm²), 22% for the heparin-MA (3×75 cm²) and less than 20% for the Q75-MA (75 cm²), D75-MA (75 cm²), SC-MA (75 cm²) and the 3 ml Cellufine® sulfate column. Prior to sample loading, the chromatography material was equilibrated with sample buffer (100 mM citric acid, pH 7.2). After a brief washing the adsorbed virus particles were eluted with elution buffer (100 mM citric acid, 2 M NaCl, pH 7.2). Resulting fractions were pooled and analyzed for virus and contaminant compositions. Chromatographic materials were regenerated after each run with 10 column volumes of 1 M NaOH and 0.1 M HCl in 1 M NaCl. Dynamic binding studies were performed in triplicates for Cellufine® sulfate and the heparin-MA and once for all other materials (Table 2). All other experiments were performed at least in triplicates, the precise number of experiments is indicated in FIG. 1A.

TABLE 2

Dynamic binding capacity of the tested chromatography materials.

| Chromatography Media | Functional Groups | N | Breakthrough Volume (ml) | Total $TCID_{50}$ ($TCID_{50}$) |
|---|---|---|---|---|
| Q75-MA | Quaternary ammonium | 3 | >20 | >9.3 × 10⁸ |
| D75-MA | Diethylamine | 3 | >20 | >9.3 × 10⁸ |
| S75-MA | Sulfonic acid | 3 | 2.5 | 1.2 × 10⁸ |
| C75-MA | Carboxyl | 3 | 2.7 | 1.3 × 10⁸ |
| Heparin-MA | Heparin | 3 | 6.0 | 2.8 × 10⁸ |
| SC-MA | Sulfated cellulose (~20 μg/g dry membrane) | 3 | >20 | >9.3 × 10⁸ |
| Toyopearl ® AF-Heparin (3 ml) | Heparin | 3 | 3.0 | 1.4 × 10⁸ |
| Cellufine ® sulfate (3 ml) | Sulfated cellulose (≧700 μg/g dry gel) | 3 | >20 | >9.3 × 10⁸ |

The adsorption area of all membrane adsorbers was 75 cm². The applied buffer was 100 mM citric acid (pH 7.2).

Combination of Membrane Adsorbers

The chromatography was performed using the same system and monitored as described above. All membrane adsorbers were equilibrated with sample buffer (100 mM citric acid, pH 7.2) before virus adsorption. Six ml of the clarified MVA-BN® virus sample were subjected to a SC-MA (75 cm²) or a heparin-MA (225 cm²) at a flow rate of 10 ml/min. After a brief washing (sample buffer, 10 ml/min) the adsorbed virus particles were eluted (100 mM citric acid, 2 M NaCl, pH 7.2; 0.5 ml/min), pooled and dialysed against sample buffer with a MWCO of 5000 kDa (Cat.# 131192, Spectrum Europe B.V., Netherlands). Dialysed samples were further purified via a Q75-MA (75 cm²; FIG. 2) applying identical operating conditions as for the pseudo-affinity MA, except for the adsorption flow rate of 0.5 ml/min.

The virus content and the amount of total dsDNA and protein were determined from a representative sample as described above. Analytical samples removed were considered in the overall mass balances.

Separation of MVA-BN® by Membrane Adsorption Chromatography and Cellufine® Sulfate Column Chromatography Both tested anion exchange MA (Q75-MA and D75-MA) had a dynamic binding capacity of >20 ml culture broth capturing MVA-BN® virus particles (Table 2). Comparable dynamic binding capacities (>20 ml) were achieved by the sulfated cellulose based pseudo-affinity matrices (SC-MA and 3 ml Cellufine® sulfate column). A reduced capacity of 6.0 ml and 3.0 ml was observed for the heparin matrices, the heparin-MA and the 3.0 ml Toyopearl AF-Heparin column, respectively. The tested cation exchange MA, S75-MA and C75-MA, resulted in a dynamic binding capacity of 2.5 ml and 2.7 ml, respectively.

Due to the low dynamic binding capacity of the 3 ml Toyopearl® AF-Heparin column and the S75-MA these matrices were not further characterized. Studies with the C-75-MA were continued despite the low dynamic binding capacity to compare the performance of a weak cation exchanger with the negatively charged pseudo-affinity MA. To increase the capacity of the C75-MA and heparin-MA, three 75 cm² units were serially combined to obtain an overall adsorption area of 225 cm².

Viruses have been shown to bind sulfated polysaccharides such as dextran sulfate, heparin, and heparan sulphate (Lycke et al., J Gen Virol 72(5):1131-1137, 1991; Mitsuya et al. 1988; O'Keeffe et al., Biotechnology and Bioengineering 62(5):537-545, 1999; O'Neil et al., 1993; Opitz et al. 2009).

Here, a significant difference in the dynamic binding capacities for the tested heparin and sulfated cellulose matrices was observed. However, the heparin density, the average molecular weight of the heparin ligands as well as their degree and type of sulfation are not provided from the respective manufacturers. These parameters can play a role for the heparin target interaction (Feyzi et al., J. Biol. Chem. 272(40):24850-24857, 1997; Marks et al., Journal of Medicinal Chemistry 44(13):2178-2187, 2001; Rusnati et al., J. Biol. Chem. 272 (17):11313-11320 1997).

Further investigations of the ion exchange MA for the capturing of MVA-BN® virus particles revealed that a fraction of MVA-BN® virus particles (21%; FIG. 1A) adsorbed to the weak cation exchanger C75-MA and was desorbed by an increased ionic strength via NaCl. A similar result, even more pronounced, was described by Opitz et al. for purification of cell culture-derived influenza virus particles (Opitz et al. 2009). The overall pI of influenza virus particles as judged by the subtype $A_2$/Singapore/57 (5.0; Zhilinskaya et al., Acta Virol. 16(5):436-439, 1972) is less acidic than the pI of Vaccinia virus particles. Nevertheless, based on their overall pI both types of viruses are not expected to bind at neutral buffer conditions to cation exchangers. However, the surface charge of larger particles (i.e. virions) influences significantly their adsorption behaviour. This might explain the adsorption characteristics of MVA-BN® and influenza virus particles to cation exchange matrices.

The virus content in the product fraction of the Q75-MA and D75-MA was 77% and 72% of the initial MVA-BN® virus (FIG. 1A). Fourteen to 17% of the virus particles did not adsorb to the matrices. In addition, for both anion exchange MA the overall virus balance could not be closed and a small portion of the initial virus particles could not be accounted for. Those particles could presumably not be desorbed during the elution but only during the following regeneration. Incomplete desorption of virus particles was also described for cell culture-derived influenza virus particles from two anion exchange MA (i.e. Q75-MA and D75-MA) (Kalbfuss et al. 2007), supporting the observations described here. These losses might be due to strong adsorption of virus sub-fractions or virus debris, which are accounted for in the analytics. Alternatively, the losses may be explained by a filtration effect of MA, which is particularly relevant in the case of large virus aggregates. However, if the appropriate membrane pore size has been selected for the virus particles, product losses due to filtration effects are minimal as can be judged from high virus recoveries observed by Opitz et al. after a SC-MA capture of influenza virus particles (Opitz et al. 2009). Furthermore, unspecific product losses have also been described in the literature for proteins during membrane chromatography (Sorci et al., Desalination 199(1-3):550-552, 2006). Hence, the observed losses of MVA-BN® virus particles are not necessarily related to the particle size.

Figure 1B:
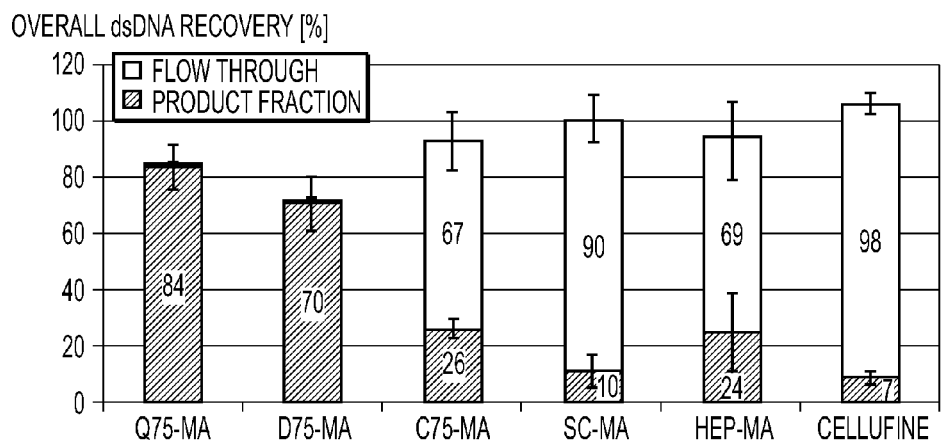

One striking drawback of anion exchange MA was the co-adsorption of dsDNA. Vaccinia viruses have a double-stranded DNA genome (Antoine et al., Virology 244(2):365-396, 1998). Hence differentiation between host cell DNA and virus DNA cannot be accomplished by the applied total DNA assay. However, after host cell homogenization it is evident, that only a minor fraction of the measured total dsDNA is viral DNA. Pooled product fractions of the Q75-MA and D75-MA contained 84% and 70% dsDNA, respectively (FIG. 1B). Kalbfuss et al. established a NaCl step gradient for a bead-based anion exchanger, which allowed the separation of influenza virus particles from the contaminating host cell DNA during the desorption process (Kalbfuss et al., Biotechnology and Bioengineering 96(5):932-944, 2007). This was not possible for MVA-BN® virus particles and the host cell DNA of primary CEF cells with the applied MA (data not shown). Hence, the product fraction was heavily contaminated with dsDNA (FIG. 1B). However, some of the adsorbed dsDNA was not desorbed during the elution process. This dsDNA was either desorbed during the regeneration or bound irreversibly to the MA, allowing a remote reduction of dsDNA in the product fraction. Similar studies on the purification of plasmid DNA via anion exchange membrane capsules also reported partial dsDNA losses (Syren et al. 2007). In the case of the cation exchange MA (C75-MA) dsDNA amounted to 26% in the product fraction (FIG. 1). However, virus particles also adsorbed poorly to the C75-MA, providing no possibility for an efficient separation of MVA-BN® virus particles from host cell DNA.

The advantage of an affinity adsorption process is its high specificity allowing an improved purity and a good product yield at optimal operating conditions and ligand selections. Vaccinia virus produces four different types of progeny virus from infected cells: intracellular mature virus (IMV), intracellular enveloped virus (IEV), cell-associated enveloped virus (CEV) and extracellular enveloped virus (EEV). The surface proteins differ between IMV and the other progeny virus particles. So far glycosaminoglycans have only been reported to bind to surface proteins of IMV (Ho et al. 2005; Hsiao et al. 1999; Lin et al. 2000; Resch et al., Virology 358(1):233-47, 2007; Smith, G. L. 2002, J. Gen. Virol. 83: 2915-2931). Hence, selecting heparin and sulfated cellulose matrices may lead to reduced virus yields. However, IMV is the most abundant form of the infectious progeny (Hsiao et al. 1999; Resch et al., Smith, 2002) and therefore the most prominent target for an affinity chromatography. Furthermore, it has to be considered that IMV, compared to the extracellular progeny, remains within the cell until lysis (Smith et al. 2002), pointing out the importance of cell homogenisation to achieve optimal virus yields. The possible selection of IMV via heparin and sulfated cellulose ligands might be reflected in the amount of virus which did not adsorb to the SC-MA (30%) and heparin-MA (35%; FIG. 1A). The average amount of MVA-BN® in the product fractions of the SC-MA was slightly higher with 65% compared to the heparin-MA with 56% (FIG. 1A). As before, the material balances could not be closed completely. A small fraction of the virus particles remained on the matrix and was most likely desorbed during the regeneration process. Furthermore, the bead-based Cellufine® sulfate led to comparable results for the overall virus yields (59%). Differences between the two MA and Cellufine® sulfate were observed in the depletion of dsDNA. The Cellufine® sulfate product fraction included 7% of the starting amount of dsDNA. The values for the heparin-MA and CS-MA were 24% and 10%, respectively (FIG. 1B). Hence, use of the heparin-MA resulted in at least 2 times the amount of contaminating dsDNA than use of the sulfated cellulose matrices.

Figure 1C:
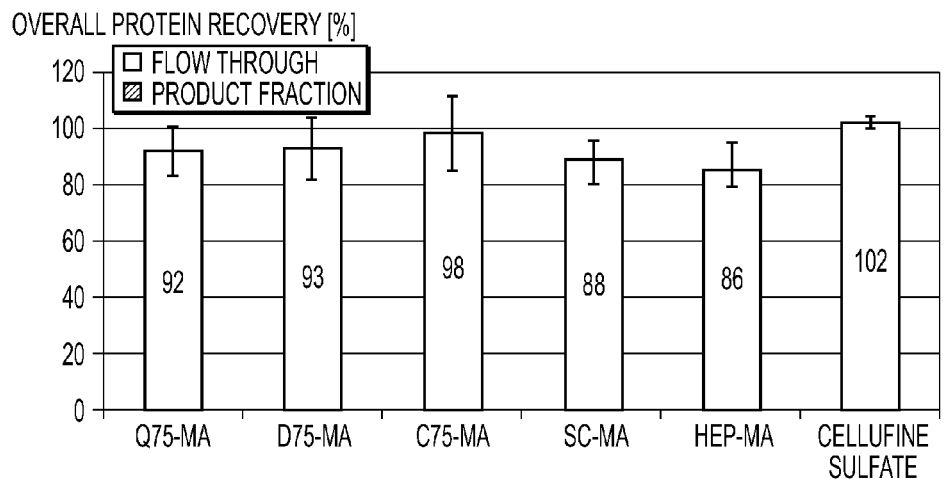

The relative amounts of total protein, based on the loaded sample, which did not adsorb to the tested matrices ranged from 86% (heparin-MA) to 102% (Cellufine® sulfate) and was in general slightly higher for the ion exchange MA (Q75-MA (92%), D75-MA (93%) and C75-MA (98%)) as compared to the pseudo-affinity MA (heparin-MA (86%) and SC-MA (88%); FIG. 1C). However, the quantity of total protein in the product fractions was below 1% in all tested chromatography materials (FIG. 1C). Hence, as observed for the virus particles and the dsDNA a small fraction of the loaded protein interacted with the tested matrices too strong to be desorbed during the elution process. Similar observations have been described by Opitz et al. during the purification of influenza virus particles (Opitz et al., Journal of Biotechnology 131(3):309-317, 2007).

Although virus recovery was slightly higher with ion exchange MA, the low level of dsDNA contamination of pseudo-affinity matrices clearly indicates a superior performance of these adsorbers to capture CEF cell-derived MVA-BN® virus particles. Furthermore, the limited dynamic binding capacities of the tested cation exchangers (S75-MA (1.5 ml) and C75-MA (2.0 ml); Tab. 1) in comparison to the sulfated cellulose matrices (Cellufine® sulfate (>20 ml) and the SC-MA (>20 ml)) are a strong indication that the interaction between the MVA-BN® particles and the SC-MA is not solely based on its negative charge. Similar observations have been reported by Opitz et al., which described significant differences for the depletion of host cell DNA from cell culture-derived influenza virus particles comparing SC-MA with weak and strong cation exchange MA (Opitz et al. 2009). On the other hand, virus yields were in their studies comparable between the SC-MA and the strong cation exchange membrane adsorber S75-MA, while virus recovery for the weak cation exchange membrane adsorber C75-MA was slightly reduced (Opitz et al. 2009). However, the improved adsorption of influenza virus particles to cation exchange resins in comparison to MVA-BN® can be explained by the reduced acidity of the influenza virus and their accessible surface charge. Hence, the observed differences in dsDNA depletion from Opitz et al. and the significant differences in the virus adsorption for cation exchange MA and the SC-MA described here support the conclusion that the interaction between MVA-BN® virus particles and sulfated cellulose was not only determined by the ionic charge of the matrix.

The main advantage of MA compared to conventional column chromatography for purification of large components (i.e. virus particles) is the reduced pressure drop, allowing operations at higher flow rates. In the case of affinity MA processes, the flow rate is mainly limited by the association and dissociation kinetics of the ligand-target complex. As shown in Table 3, an increase in flow rate from 0.5 ml/min to 10 ml/min resulted in a decrease in virus recovery for the SC-MA (14%) and the heparin-MA (12%) with a total virus recovery in the product fraction of 51% and 47%, respectively. The amount of dsDNA in the product fraction at 10 ml/min was slightly reduced compared to 0.5 ml/min for both adsorbers (Tab. 2). The recommended operating pressure (manufacture's instruction) for Cellufine® sulfate is less than 2 bar. For the applied set-up, as described in the material and methods section, this limited the flow rate to 0.5 ml/min for bead-based separations. A change in column dimensions would have allowed an increase in the flow rate for Cellufine® sulfate. However, wide column dimensions at a constant matrix volume lead to a reduced residence time, resulting in potential product losses. On the other hand, up-scaling of the complete matrix volume has to be questioned in terms of the process economics.

TABLE 3

Effect of increased flow rates on viral recovery and contaminant depletion.

| Flow Rate (ml/min) | Membrane Adsorber | MVA-BN® (%) | dsDNA (%) | Total Protein (%) |
|---|---|---|---|---|
| 0.5 | Cellufine ® sulfate | 59 ± 5.7 | 7.0 ± 1.9 | 0.2 ± 0.2 |
| 0.5 | SC-MA | 65 ± 0.5 | 6.0 ± 0.2 | <LOQ[a] |
| 5.0 | SC-MA | 54 ± 0.3 | 4.0 ± 1.0 | <LOQ[a] |
| 10.0 | SC-MA | 51 ± 0.2 | 4.0 ± 0.7 | <LOQ[a] |
| 0.5 | Heparin-MA | 59 ± 1.3 | 17 ± 2.1 | <LOQ[a] |
| 5.0 | Heparin-MA | 47 ± 3.9 | 11 ± 0.3 | <LOQ[a] |
| 10.0 | Heparin-MA | 47 ± 0.4 | 9 ± 3.1 | <LOQ[a] |

Relative amounts (mean and standard deviation of triplicates) for MVA-BN ® (ELISA), dsDNA and total protein content were calculated based on the starting material of the homogenized and clarified virus broth. The adsorption area of the SC-MA and heparin-MA was 75 cm$^2$ and 225 cm$^2$, respectively. Equilibration and wash buffer was 100 mM citric acid (pH 7.2), and the elution buffer 100 mM citric acid + 2M NaCl (pH 7.2).
[a]limit of quantification (25 µg/ml)

The overall performance based on capacity, purity, virus yield and productivity of the SC-MA was significantly better compared to ion exchange MA and heparin-MA. In terms of productivity, the SC-MA can clearly be favoured over the bead-based Cellufine® sulfate as it is possible to increase the flow rates 20-fold for the SC-MA chromatography. Furthermore, the study demonstrated that the interaction of MVA-BN® particles to sulfated cellulose is most likely not only of electrostatic nature. In fact, it has to be a complex interaction comparable to other biological affinity chromatography systems. Certainly, it should be considered that the selection of heparin and sulfated cellulose as pseudo-affinity matrix to capture MVA-BN® virus particles potentially leads to the exclusion of certain virus progenies. However, the development of a specific but virus progeny independent affinity ligand might not be justified by the low virus losses. Actually, it might be more promising to optimize the ligand density of heparin or sulfated cellulose MA.

Combination of Pseudo-Affinity and Anion Exchange Membrane Adsorbers

Regulatory expectations of host cell DNA contents in CEF-cell produced licensed vaccines are less stringent than current regulatory requirements for new vaccine products. Current guidelines for newly licensed human vaccine products from continuous cell lines stipulate that residual DNA levels exceeding 10 ng per dose are not acceptable (European-Pharmacopoeia 2009 (Version 6.4); World-Health-Organization 1998). As expected, these requirements for a new vaccine product can not be accomplished by a single initial capture step. Lowest levels for dsDNA in product fractions using MA were obtained with the SC-MA and heparin-MA. In a subsequent process step the remaining dsDNA could be eliminated by a nuclease treatment, which is routinely done via Benzonase® treatment for smallpox vaccines (Greenberg and Kennedy 2008; Monath et al. 2004) and other vaccine preparations like influenza vaccines (Wolff and Reichl, Chemical Engineering & Technology 31(6):846-857, 2008). Currently, for smallpox vaccines the Benzonase® treatments are mainly carried out after homogenization and clearance (Greenberg and Kennedy 2008; Monath et al. 2004). An application of the Benzonase® treatment in the purification scheme after the pseudo-affinity MA would significantly reduce total process costs due to the reduction of the total amount of Benzonase® required. As an alternative, the host cell DNA content could be further reduced by introduction of an additional unit operation, i.e. an anion exchange MA. Therefore, sequential capturing and purification of the MVA-BN® virus particles was explored as the next step (FIG. 2). As a result, the amount of dsDNA in the product fraction was reduced to 0.1% and 5% respectively. The overall virus recovery for the SC-MA and heparin-MA set-up was 58% and 59%, respectively. Moreover, after introduction of the subsequent anion exchange MA protein contaminations in the product fractions were reduced below the quantification limit (5 μg/ml) for both purification schemes.

On the other hand, differential elution of MVA-BN® particles and dsDNA from the Q75-MA was not possible. Both components co-eluted during a wide range of salt-concentrations (data not shown), but part of the dsDNA was desorbed during the regeneration process or bound irreversibly to the anion exchange MA (FIG. 1B). This could be exploited for a further reduction of the dsDNA content in the product fraction. Virus yields of the Q75-MA after both pseudo-affinity chromatography methods exceeded the yields obtained from loading the homogenized MVA-BN® particles directly to the Q75-MA. Virus losses were in both cases only about 4% (FIG. 2) while the dsDNA was reduced, relative to the starting material, from 4% to 0.1% for the SC-MA scheme and for the heparin-MA scheme from 23% to 5%. Other MA or purification methods could be used to further deplete the dsDNA to comply with requirements for human vaccine products. However, even if the necessary limits for host cell DNA are reached, it should be considered that a Benzonase® treatment also reduces the probability of vaccines to contain intact oncogenes or other functional DNA sequences in vaccines. (Knezevic et al., Biologicals 36(3):203-211 2008).

Pseudo-affinity MA allowed the capture of CEF cell-derived MVA-BN® at a high loading velocity (10 ml/min) with a relatively high purity. Compared to the bead-based pseudo-affinity matrix Cellufine® sulfate (0.5 ml/min), productivity could be increased by a factor of 20 with a slightly reduced product yield. The achieved purity levels, in particular the dsDNA depletion, were significantly higher for the pseudo-affinity matrices than for the tested ion exchange MA. For production of new vaccines products or virus vectors further dsDNA reduction is required and an improved viral yield would still be desirable. Preliminary experiments with SC-MA, which have been sulfated by a modified chemical reaction, indicated the potential to improve virus yields significantly. Overall, the pseudo-affinity MA represent a valuable choice to capture Vaccinia virus particles in a manufacturing process and potentially allow to economise the required Benzonase® treatment step compared to classical downstream processes for smallpox vaccines.

TABLE 1

VV surface proteins

| Surface protein (gene) | VV form | References |
|---|---|---|
| A2.5L | MV | [1] |
| A9L | MV | [2] |
| A13L | MV | [3] |
| A14L | MV | [4-7] |
| A14.5L | MV | [8] |
| A16L | MV | [9; 10] |
| A17L | MV | [11-13] |
| A21L | MV | [14] |
| A25L | MV | [15] |
| A26L | MV | [15; 16] |
| A27L | MV | [17-22] |
| A28L | MV | [23; 24] |
| A33R | EV | [25-27] |
| A34 R | EV | [28-31] |
| A36R | WV | [32-37] |
| A38L | | [38; 39] |
| A56R | EV | [40-43] |
| B5R | EV | [44-46] |
| D8L | MV | [47] |
| D13L | MV | |
| E1OR | MV | [48] |
| F9L | MV | [49] |
| F12 | WV | [37; 50] |
| F13L | EV | [51-55] |
| G3L | MV | [9] |
| G4L | MV | [56; 57] |
| G9R | MV | [9; 58] |
| H2 R | MV | [59] |
| H3L | MV | [60-62] |
| I2L | MV | [63] |
| I5L | MV | [64] |
| J5L | MV | [9] |
| K2L | WV/EV | [65-68] |
| L1R | MV | [69] |
| L5R | MV | [70] |

List of References cited in Table 1:

[1] Senkevich T G, White C L, Weisberg A, Granek J A, Wolfe E J, Koonin E V, Moss B: Expression of the vaccinia virus A2.5L redox protein is required for virion morphogenesis. Virology 2002; 300(2): 296-303.
[2] Yeh W W, Moss B, Wolfe E J: The vaccinia virus A9L gene encodes a membrane protein required for an early step in virion morphogenesis. J Virol 2000; 74(20): 9701-9711.
[3] Unger B, Traktman P: Vaccinia virus morphogenesis: a13 phosphoprotein is required for assembly of mature virions. J Virol 2004; 78(16): 8885-8901.
[4] Traktman P, Liu K, DeMasi J, Rollins R, Jesty S, Unger B: Elucidating the essential role of the A14 phosphoprotein in vaccinia virus morphogenesis: construction and characterization of a tetracycline-inducible recombinant. J Virol 2000; 74(8): 3682-3695.
[5] Rodriguez J R, Risco C, Carrascosa J L, Esteban M, Rodriguez D: Vaccinia virus 15-kilodalton (A14L) protein is essential for assembly and attachment of viral crescents to virosomes. J Virol 1998; 72(2): 1287-1296.
[6] Mercer J, Traktman P: Investigation of structural and functional motifs within the vaccinia virus A14 phosphoprotein, an essential component of the virion membrane. J Virol 2003; 77(16): 8857-8871.
[7] Betakova T, Wolffe E J, Moss B: Regulation of vaccinia virus morphogenesis: phosphorylation of the A14L and A17L membrane proteins and C-terminal truncation of the AI 7L protein are dependent on the F1OL kinase. J Virol 1999; 73(5): 3534-3543.
[8] Betakova T, Wolffe E J, Moss B: The vaccinia virus A14.5L gene encodes a hydrophobic 53-amino-acid virion membrane protein that enhances virulence in mice and is conserved among vertebrate poxviruses. J Virol 2000; 74(9): 4085-4092.
[9] Senkevich T G, Ojeda S, Townsley A, Nelson G E, Moss B: Poxvirus multiprotein entry-fusion complex. Proc Natl Acad Sci USA 2005; 102(51): 18572-18577.
[10] Ojeda S, Senkevich T G, Moss B: Entry of vaccinia virus and cell-cell fusion require a highly conserved cysteine-rich membrane protein encoded by the AI 6L gene. J Virol 2006; 80(1): 51-61.
[11] Betakova T, Wolfe E J, Moss B: Membrane topology of the vaccinia virus A17L envelope protein. Virology 1999; 261(2): 347-356.
[12] Rodriguez D, Esteban M, Rodriguez J R: Vaccinia virus A17L gene product is essential for an early step in virion morphogenesis. J Virol 1995; 69(8): 4640-4648.
[13] Wolffe E J, Moore D M, Peters P J, Moss B: Vaccinia virus A17L open reading frame encodes an essential component of nascent viral membranes that is required to initiate morphogenesis. J Virol 1996; 70(5): 2797-2808.
[14] Townsley A C, Senkevich T G, Moss B: Vaccinia virus A21 virion membrane protein is required for cell entry and fusion. J Virol 2005; 79(15): 9458-9469.
[15] Ulaeto D, Grosenbach D, Hruby D E: The vaccinia virus 4c and A-type inclusion proteins are specific markers for the intracellular mature virus particle. J Virol 1996; 70(6): 3372-3377.
[16] McKelvey T A, Andrews S C, Miller S E, Ray C A, Pickup D J: Identification of the orthopoxvirus p4c gene, which encodes a structural protein that directs intracellular mature virus particles into A-type inclusions. J Virol 2002; 76(22): 11216-11225.
[17] Ho Y, Hsiao J C, Yang M H, Chung C S, Peng Y C, Lin T H, Chang W, Tzou D L: The oligomeric structure of vaccinia viral envelope protein A27L is essential for binding to heparin and heparan sulfates on cell surfaces: a structural and functional approach using site-specific mutagenesis. J Mol Biol 2005; 349(5): 1060-1071.
[18] Vazquez M I, Esteban M: Identification of functional domains in the 14- kilodalton envelope protein (A27L) of vaccinia virus. J Virol 1999; 73(11): 9098-9109.
[19] Hsiao J C, Chung C S, Chang W: Cell surface proteoglycans are necessary for A27L protein-mediated cell fusion: identification of the N-terminal region of A27L protein as the glycosaminoglycan-binding domain. J Virol 1998; 72(10): 8374-8378.
[20] Chung C S, Hsiao J C, Chang Y S, Chang W: A27L protein mediates vaccinia virus interaction with cell surface heparan sulfate. J Virol 1998; 72(2): 1577-1585.
[21] Vazquez M I, Rivas G, Cregut D, Serrano L, Esteban M: The vaccinia virus 14-kilodalton (A27L) fusion protein forms a triple coiled-coil structure and interacts with the 21-kilodalton (A17L) virus membrane protein through a C-terminal alpha-helix. J Virol 1998; 72(12): 10126-10137.
[22] Rodriguez D, Rodriguez J R, Esteban M: The vaccinia virus 14-kilodalton fusion protein forms a stable complex with the processed protein encoded by the vaccinia virus AI 7L gene. J Virol 1993; 67(6): 3435-3440.
[23] Senkevich T G, Ward B M, Moss B: Vaccinia virus entry into cells is dependent on a virion surface protein encoded by the A28L gene. J Virol 2004; 78(5): 2357-2366.
[24] Senkevich T G, Ward B M, Moss B: Vaccinia virus A28L gene encodes an essential protein component of the virion membrane with intramolecular disulfide bonds formed by the viral cytoplasmic redox pathway. J Virol 2004; 78(5): 2348-2356.
[25] Roper R L, Wolffe E J, Weisberg A, Moss B: The envelope protein encoded by the A33R gene is required for formation of actin-containing microvilli and efficient cell-to-cell spread of vaccinia virus. J Virol 1998; 72(5): 4192-4204.
[26] Roper R L, Payne L G, Moss B: Extracellular vaccinia virus envelope glycoprotein encoded by the A33R gene. J Virol 1996; 70(6): 3753-3762.
[27] Wolffe E J, Weisberg A S, Moss B: The vaccinia virus A33R protein provides a chaperone function for viral membrane localization and tyrosine phosphorylation of the A36R protein. J Virol 2001; 75(1): 303-310.
[28] Duncan S A, Smith G L: Identification and characterization of an extracellular envelope glycoprotein affecting vaccinia virus egress. J Virol 1992; 66(3): 1610-1621.
[29] Rottger S, Frischknecht F, Reckmann I, Smith G L, Way M: Interactions between vaccinia virus IEV membrane proteins and their roles in IEV assembly and actin tail formation. J Virol 1999; 73(4): 2863-2875.

We claim:

1. An industrial-scale method for the purification of biologically active Vaccinia viruses comprising:
    i) loading a solid-phase matrix comprising a sulfated cellulose with biologically active Vaccinia viruses, wherein the solid-phase matrix comprises or is a membrane;
    ii) washing the matrix; and
    iii) eluting a minimum of $5.0 \times 10^{12}$ Vaccinia virus particles.

2. The method of claim 1, wherein the Vaccinia viruses are recombinant Vaccinia viruses.

3. The method of claim 1, wherein the Vaccinia viruses are modified Vaccinia Ankara viruses or recombinant modified Vaccinia Ankara viruses.

4. The method of claim 1, wherein the solid-phase matrix comprises a membrane.

5. The method of claim 1, wherein the solid-phase matrix is a membrane.

6. The method of claim 4, wherein the solid-phase matrix comprises a sulfated reinforced cellulose membrane.

7. The method of claim 4, wherein the solid-phase matrix is a sulfated reinforced cellulose membrane.

8. The method of claim 1, wherein the Vaccinia viruses are eluted with sodium chloride (NaCl).

9. The method of claim 1, additionally comprising a purification step by ion-exchange.

10. The method of claim 9, wherein the purification step by ion-exchange comprises a membrane.

11. The method of claim 1, further comprising administering the eluted Vaccinia viruses to an animal.

12. The method of claim 11, wherein the animal is a human.

13. An aseptic method for the purification of biologically active Vaccinia virus comprising:
    i) aseptically loading a solid-phase matrix comprising a sulfated cellulose with a biologically active Vaccinia virus, wherein the solid-phase matrix comprises or is a membrane;
    ii) aseptically washing the matrix; and
    iii) aseptically eluting the biologically active Vaccinia virus.

14. The method of claim 13, wherein the Vaccinia virus is a recombinant Vaccinia virus.

15. The method of claim 13, wherein the Vaccinia virus is a modified Vaccinia Ankara virus or a recombinant modified Vaccinia Ankara virus.

16. The method of claim 13, wherein the solid-phase matrix comprises a membrane.

17. The method of claim 13, wherein the solid-phase matrix is a membrane.

18. The method of claim 16, wherein the solid-phase matrix comprises a sulfated reinforced cellulose membrane.

19. The method of claim 16, wherein the solid-phase matrix is a sulfated reinforced cellulose membrane.

20. The method of claim 13, wherein the Vaccinia virus is eluted with sodium chloride (NaCl).

21. The method of claim 13, additionally comprising a purification step by ion-exchange.

22. The method of claim 21, wherein the purification step by ion-exchange comprises a membrane.

23. The method of claim 13, further comprising administering the eluted Vaccinia virus to an animal.

24. The method of claim 23, wherein the animal is a human.

* * * * *